US005736528A

United States Patent [19]
Belardinelli et al.

[11] Patent Number: 5,736,528
[45] Date of Patent: Apr. 7, 1998

[54] $N^6$-(EPOXYNORBORN-2-YL) ADENOSINES AS $A_1$ ADENOSINE RECEPTOR AGONISTS

[75] Inventors: Luiz Belardinelli, Gainesville; Ray Olsson, Tampa; Stephen Baker, Gainesville, all of Fla.; Peter J. Scammells, Highton, Australia; Peter G. Milner; Jürg R. Pfister, both of Los Altos, Calif.

[73] Assignee: University of Florida Research Foundation, Inc., Gainesville, Fla.

[21] Appl. No.: 581,655

[22] Filed: Dec. 29, 1995

Related U.S. Application Data

[63] Continuation-in-part of Ser. No. 330,640, Oct. 28, 1994, Pat. No. 5,631,260, which is a continuation-in-part of Ser. No. 144,459, Oct. 28, 1993, Pat. No. 5,446,046.

[51] Int. Cl.$^6$ ............... A61K 31/70; C07H 19/167
[52] U.S. Cl. ............... 514/46; 514/821; 536/27.62
[58] Field of Search ............... 514/46, 821; 536/27.62

[56] References Cited

U.S. PATENT DOCUMENTS

| | | | |
|---|---|---|---|
| 3,998,953 | 12/1976 | Konz et al. | 514/263 |
| 4,364,922 | 12/1982 | Berne et al. | 424/9 |
| 4,713,455 | 12/1987 | Furrer et al. | 544/267 |
| 4,980,379 | 12/1990 | Belardinelli et al. | 514/821 |
| 5,288,721 | 2/1994 | Klein et al. | 514/263 |

FOREIGN PATENT DOCUMENTS

| | | |
|---|---|---|
| 0374808 | 6/1990 | European Pat. Off. |
| 0415456 | 3/1991 | European Pat. Off. |
| 4205306 | 8/1993 | Germany |
| 9200297 | 1/1992 | WIPO |
| 9416702 | 8/1994 | WIPO |

OTHER PUBLICATIONS

Belardinelli, L., J. Linden, R.M. Berne (1989) "The Cardiac Effects of Adenosine" Progress in Cardiovascular Diseases 32(1):73–97.

Belardinelli, L., A. Pelleg (1990) "Cardiac Electrophysiology and Pharmacology of Adenosine" Journal of Cardiovascular Electrophysiology 1(4):327–339.

Olsson, R.A., J.D. Pearson (1990) "Cardiovascular Purinoceptors" Physiological Reviews 70(3):761–845.

Belardinelli, L. (1993) "Adenosine System in the Heart" Drug Development Research 28:263–267.

Belardinelle, L. (1991) "Adenosine: Cardiac Electrophysiology" Pacing and Clinical Electrophysiology 14(11):1672–1680.

Jacobson, K.A. et al. (1992) "Adenosine Receptors: Pharmacology, Structure–Activity Relationships, and Therapeutic Potential" Journal of Medicinal Chemistry 35(3):407–422.

*Primary Examiner*—Gary L. Kunz
*Attorney, Agent, or Firm*—Saliwanchik, Lloyd & Saliwanchik

[57] ABSTRACT

$N^6$-(epoxynorborn-2-yl)adenosines are A1 adenosine receptor agonists that are useful for controlling atrial fibrillation, ventricular rate in atrial flutter, supraventricular tachyarrhythmia, inhibiting A—V- nodal transmission in supraventricular tachycardia, and for normalizing ventricular rhythm and hemodynamics.

10 Claims, 10 Drawing Sheets

$N^6$-(EPOXYNORBORN-2-YL) ADENOSINES AS $A_1$ ADENOSINE RECEPTOR AGONISTS

CROSS-REFERENCE TO A RELATED APPLICATION

This application is a continuation-in-part of application Ser. No. 08/330,640, filed Oct. 28, 1994, now U.S. Pat. No. 5,631,260; which is a continuation-in-part of application Ser. No. 08/144,459, filed Oct. 28, 1993, now U.S. Pat. No. 5,446,046.

BACKGROUND OF THE INVENTION

Adenosine is an extracellular messenger generated by all cells in the body. Adenosine itself, substances that mimic the actions of adenosine, and substances that antagonize its actions have important clinical applications. In the heart, an organ whose function depends critically on an adequate supply of oxygen, adenosine regulates the balance between oxygen supply (coronary blood flow) and oxygen demand (cardiac work). Adenosine released from working heart cells increases oxygen supply through coronary dilation and decreases oxygen consumption by slowing heart rate and modulating β-adrenergic stimulation. The protective effects of adenosine are particularly important when cardiac oxygen supply is limited, for example, by coronary artery narrowing.

Several recent reviews describe the adenosine system in detail (Belardinelli, L., J. Linden, R. M. Berne [1989] Prog. Cardiovasc. Dis. 32:73–97; Belardinelli, L., A. Pelleg [1990] J. Cardiovasc. Electrophysiol. 1:327–339; Olsson, R. A., J. D. Pearson [1990] Physiol. Rev. 70:761–845). The cardiac adenosine system consists of three processes: (1) mechanisms for adenosine formation; (2) adenosine receptors and proteins that couple them to effectors; and (3) mechanisms for the removal of adenosine. Selective modification of one or more of these systems by means of drugs such as adenosine receptor antagonists and adenosine uptake inhibitors can modify the actions of adenosine for therapeutic benefit.

Adenosine formation increases when oxygen demand exceeds its supply, thereby promoting the degradation of adenine nucleotides. The degradation of adenylates released from nerve terminals along with neurotransmitters and the degradation of S-adenosylhomocysteine, a byproduct of methylation reactions, are additional sources of adenosine in the heart. Heart muscle and coronary blood vessel cells take up very nearly all the adenosine generated in the heart, reincorporating that adenosine into the cellular nucleotide pool.

At least two types of receptors mediate the actions of adenosine in the heart. $A_1$ adenosine receptors ($A_1AR$) decrease oxygen consumption, for example, by slowing heart rate, and $A_2$ adenosine receptors ($A_2AR$) increase oxygen supply by causing coronary vasodilation. The actions of adenosine on cardiac cells are either direct (cAMP-independent) or indirect (cAMP-dependent). The direct actions include the negative dromotropic effect on the AV node. Those electrophysiological effects are the basis of adenosine's anti-arrhythmic properties; adenosine is highly effective (>90%) in terminating paroxysmal supraventricular tachycardia (PSVT). The $A_1AR$-mediated inhibition of agonist-stimulated (but not basal) adenylate cyclase activity constitutes the indirect effects of adenosine. Whereas the direct effects of adenosine occur in the absence of agents that act through adenylate cyclase, the indirect effects reflect the inhibition of this enzyme when it is stimulated by agents such as β-adrenergic agonists.

A number of pharmacological studies employing receptor-selective agonists support the idea that $A_2ARs$ mediate coronary vasodilation. Although endothelial cells contain $A_2ARs$ and thus could play a role in vasodilation, they are not essential, for adenosine acts on coronary smooth muscle cells, causing them to relax.

When adenosine is used as a drug, its side effects are usually transitory, a reflection of its extremely rapid degradation in the body (seconds). The safety of adenosine in the diagnosis and treatment of PSVT is now well established. An important factor which has inhibited the therapeutic development of the adenosine analogs is the ubiquitous nature of adenosine's action on a variety of tissues.

Two kinds of drugs modify the actions of adenosine according to whether they magnify or attenuate the effects of the nucleoside. Inhibitors of the cell membrane nucleoside transporter block the removal of adenosine from the extracellular space, thereby increasing its concentration and intensifying its action. Adenosine uptake blockers also inhibit the nucleoside transport system in human erythrocytes and cardiocyte membranes and potentiate the cardiac actions of adenosine in the dog.

Methylxanthines competitively antagonize the binding of adenosine to both the $A_1AR$ and the $A_2AR$. Certain naturally occurring methylxanthines such as caffeine and theophylline antagonize the cardiovascular effects of adenosine. For example, the administration of adenosine to patients receiving theophylline fails to produce AV block or terminate PSVT. However, those methylxanthines are relatively weak and, more importantly, are nonselective, antagonizing both the electrophysiological and vasodilatory effects of adenosine in laboratory animals and humans. Theophylline also ameliorates the non-cardiac effects of adenosine such as flushing, local pain, and respiratory stimulation.

Synthetic alkylxanthines, e.g., 8-cyclopentyl-1,3-dipropylxanthine (CPX; see U.S. Pat. Nos. 4,364,922 and 4,980,379), are significantly more potent and selective antagonists at the $A_1AR$ than are theophylline or caffeine.

BRIEF SUMMARY OF THE INVENTION

The present invention concerns the discovery of certain novel compounds which can bind to adenosine receptors with surprisingly high affinity, specificity, and selectivity. Specifically exemplified herein are xanthine and adenosine analogs comprising an epoxide moiety. As explained in more detail herein, these adenosine agonists and antagonists have therapeutic utility in a broad range of applications including cardiac and renal regulation. Included among these novel compounds are both adenosine agonists and antagonists.

In one embodiment of the subject invention, the novel compound known as 1,3-dipropyl-8-{3-oxatricyclo[3.1.2.0$^{2,4}$]oct-6(7)-yl}xanthine, herein referred to as ENX, is used as an antagonist of adenosine. Advantageously, ENX has been found to be uniquely potent, specific, and highly selective for the $A_1$ adenosine receptor. Particular enantiomers of the ENX compound were synthesized and tested for their relative activity. Testing of R-and S-enantiomers of ENX revealed advantages of the S-enantiomers, namely, potency and selectivity for the $A_1AR$ greater than those of the racemate or the R-enantiomer. However, the R-enantiomer, by virtue of its shorter biological half-life, can be advantageous in defined therapeutic applications requiring a short duration of action.

The subject invention further concerns other xanthines and adenosines comprising an epoxide moiety in an exocyclic substituent. Further embodiments of the invention include compositions and formulations comprising ENX or those analogs or derivatives which can have therapeutic utility as agonists or antagonists of adenosine.

A further aspect of the subject invention is a method for using the disclosed compounds for modulating the biological activity of adenosine. The compounds, or compositions comprising those compounds, can be utilized for their modulating effect on adenosine, e.g., as agonists or antagonists of adenosine receptors. The antagonist activity of the subject compounds can be utilized in treating conditions where elevated levels of adenosine are present; the agonists can be useful where stimulation of the adenosine receptor is needed. Such conditions include, but are not limited to, cardiac, renal, hepatic, or lung diseases, such as cardiac arrhythmias, renal failure, liver failure ascites, and asthma. Modulating adenosine activity can also be used in the treatment of maturity onset diabetes.

Certain $N^6$-substituted adenosine compounds have also been discovered to have activity as $A_1$ adenosine receptor agonists. Both racemic exo- and endo- isomers of $N^6$-(5,6-epoxynorborn-2-yl) adenosine have been synthesized and shown to be both potent and highly selective agonists for the $A_1$ adenosine receptor. In the preparation of these compounds, exo- and endo- norbornenylamines can be synthesized and are accessed through an optimized Curtius rearrangement.

Novel methods of synthesizing compounds of the subject invention are also described and considered as part of the invention.

BRIEF DESCRIPTION OF THE DRAWINGS

FIGS. 4A–4B show an analog record of the prolongation of the S—H interval ($A_1$ response, FIG. 4A) and the increase in coronary conductance ($A_2$ response, FIG. 4B) caused by a 3 minute infusion of adenosine (4 µM) in the absence and presence of 0.4 µM ENX. ENX inhibited the negative dromotropic effect of adenosine, but did not antagonize the coronary vasodilation (increase in coronary conductance) caused by adenosine. FIGS. 4C–4D show selective antagonism by ENX (0.4 µM) of the $A_1$ receptor-mediated increase in the S—H interval caused by adenosine (4 µM), but not the $A_2$ receptor mediated coronary vasodilation. The values are the mean±SEM from five guinea pig hearts. The asterisk is indicated by those values significantly different from adenosine alone (P<0.05).

FIG. 9A shows a scheme heretofore previously undescribed; FIG. 9B shows the standard scheme for production of the exo-5-norborn-2-ene.

DETAILED DESCRIPTION OF THE DISCLOSURE

The subject invention pertains to novel compounds, and formulations comprising those compounds, and methods of synthesizing the compounds. The compounds or compositions of the subject invention can advantageously be used as either agonists or antagonists at adenosine receptors. Specifically, these compounds either promote or antagonize the negative dromotropic, chronotropic, and inotropic effects mediated by an $A_1$ adenosine receptor ($A_1$AR). In the heart, these compounds can either promote or antagonize the negative dromotropic, chronotropic, and inotropic effects mediated by $A_1$AR, and in the kidney the antagonists promote diuresis through an $A_1$AR.

The subject compounds are of two general types: (1) 1,3-dialkylxanthines having C-8 substituents that comprise an epoxide (oxiranyl) moiety, and (2) adenosines having N-6 substituents that comprise an epoxide moiety. In a preferred embodiment of the subject invention, the xanthine epoxides are 1,3-dialkylxanthines having an epoxide moiety covalently bound to the C-8 substituent of xanthine. The preferred epoxides of xanthine or adenosine are those having an epoxide moiety as part of an exocyclic substituent.

The general structure of one class of 1,3-dialkylxanthines is shown below as Formula I:

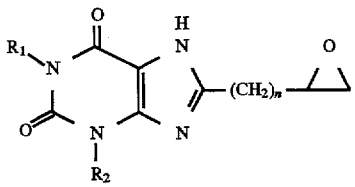

(I)

wherein $R_1$ and $R_2$ are the same or different, and can be an alkyl group of 1–4 carbons in length; and n=0–4. It would also be understood that $R_1$ and/or $R_2$ can be a hydrogen. Compounds which have one of the R-groups as hydrogen and the other R-group as an alkyl would be epoxides of alkyl xanthine; compounds having both R-groups as alkyls are epoxides of dialkylxanthine.

The general structure of the 1,3-dialkyl-8-oxatricycloalkylxanthines is shown below as Formula II:

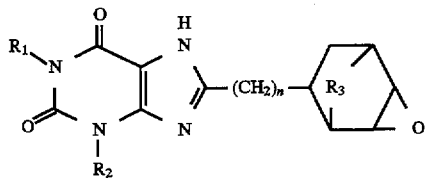

(II)

wherein $R_1$ and $R_2$ are the same or different, and can be a hydrogen or an alkyl group of 1–4 carbons; $R_3$ is either O or an alkyl group of 1–4 carbons; and n=0–4.

A polymethylene chain 1–4 carbons in length can link the epoxide moiety to C-8 of 1,3-dialkylxanthine, as in Formula I. The epoxide group can also be part of an exocyclic substituent linked to C-8 of the xanthine moiety, either directly or through a (poly)methylene chain 1–4 carbons long, as in Formula II. The exocyclic substituent, shown as Formula II, can be a bicycloalkyl group, forming an oxatricycloalkyl substituent. Other exocyclic epoxide structures can also be part of the compound as would be readily recognized by those skilled in the art having the benefit of this disclosure. The bicycloalkyl group can further contain an alkenyl group for the formation of a second epoxide moiety.

Figure 1:
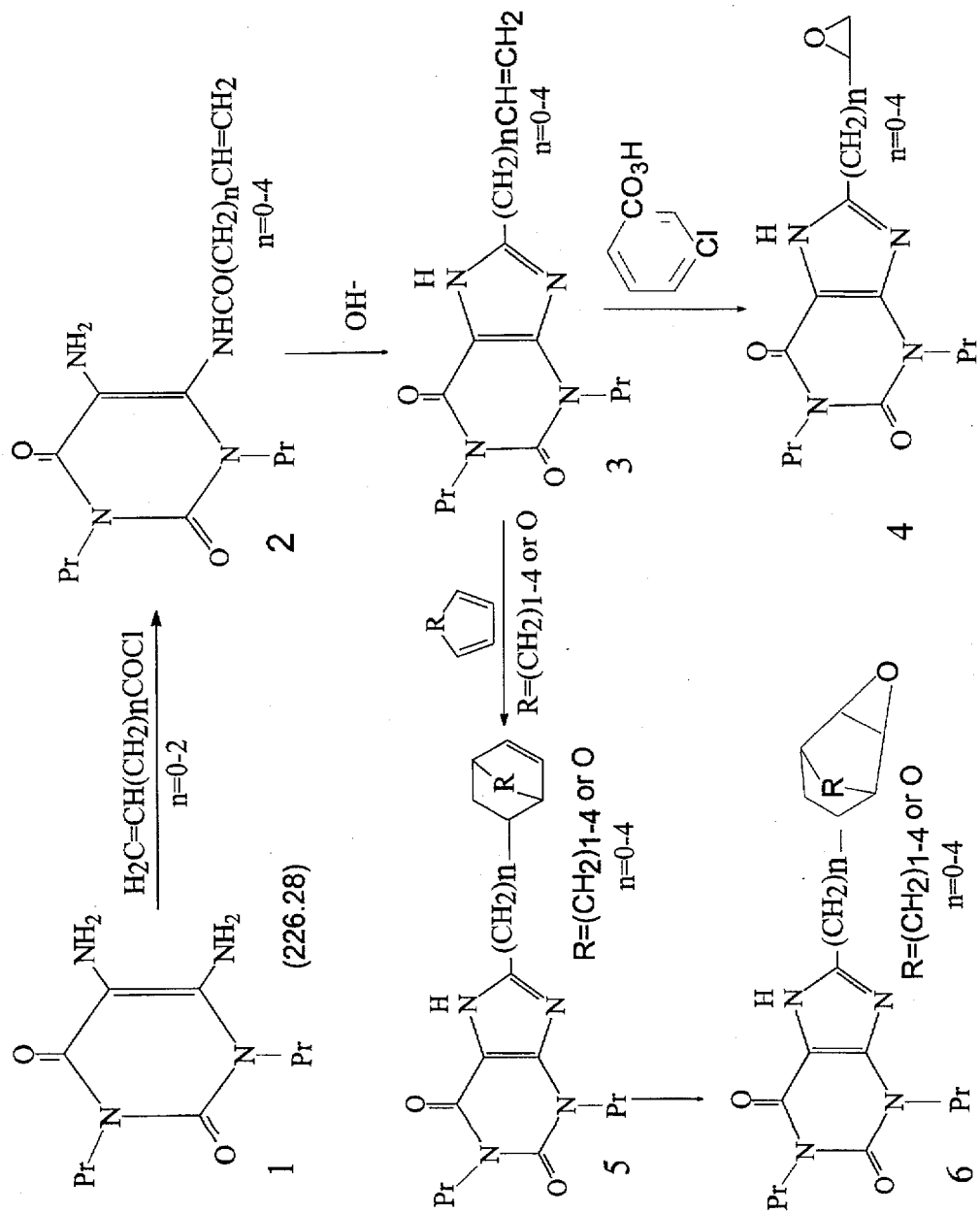
FIG. 1 shows a scheme outlining the syntheses of 1,3-dipropylxanthines having C-8 substituents that contain an epoxide moiety.

FIG. 1 depicts a general synthesis scheme for the 8-substituted 1,3-dipropylxanthines.

One preferred embodiment of the subject invention is a compound having the chemical name 1,3-dipropyl-8-{3-oxatricyclo[3.1.2.0$^{2,4}$]oct-6(7)-yl}-xanthine, which is commonly termed epoxynorbornylxanthine, or ENX. The formula for ENX is shown as Formula III, below:

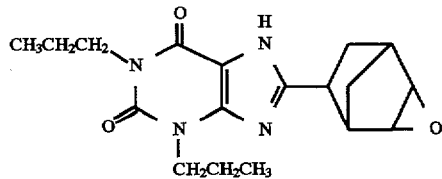

(III)

ENX has been demonstrated to have advantageous and unexpected properties as an adenosine antagonist by its high selectivity and affinity for the $A_1$ adenosine receptor.

Essentially, a patient who has any condition where levels of endogenous adenosine are, or could become, excessive can benefit from therapeutic use of the subject antagonist compound or a composition comprising the compound. For example, the subject invention pertains to the use of the subject antagonist compounds as diuretics or in the treatment of renal failure. In addition, the subject antagonist compounds or compositions comprising these compounds can be employed in the treatment of certain conditions affecting the heart, including bradyarrhythmias associated with hypoxia or ischemia (myocardial infarction), sick sinus node syndrome, and in heart failure, where the positive inotropic effect of the antagonist can be advantageous. Other conditions which are recognized as resulting from, or affected by, elevated levels of endogenous adenosine can also be treated with the subject adenosine antagonists.

The high selectivity and affinity for $A_1$ adenosine receptor exhibited by the subject compounds, e.g., ENX, make them particularly useful as diuretics. The potency of ENX as a diuretic has been demonstrated to be at least as high as the potency of furosemide (Lasix), a commonly used diuretic in human and animal medicine. Thus, it would be understood that ENX could be used in a manner comparable to the way furosemide is used to produce a diuretic effect in a patient.

The diuretic activity exhibited by ENX can be exploited in the treatment of several conditions commonly affecting mammals, especially humans. For example, congestive heart failure (CHF) is a condition in which diuretics are extensively used. Hypertension, often a concurrent condition with CHF, is also regularly treated with diuretics. ENX was shown to have comparable diuretic activity and potency as currently marketed diuretics, e.g., Lasix, used for treatment of such conditions. Thus, the subject compounds, especially ENX, can be used in a similar manner for treatment of these conditions.

The subject adenosine antagonists can also be indicated as nephroprotecting compounds. ENX, which has been shown to bind to the $A_1$ adenosine receptor, can be used to block those receptors during the use of contrast agents known to be nephrotoxic, or can be useful in treatments to counteract the nephrotoxic effects of certain antibiotics, e.g., gentamycin, amphotericin, or cyclosporin.

In addition, the subject $A_1$ adenosine antagonists, e.g., ENX, can be useful for treatment of the ascites of liver failure. As would be readily understood in the art, ENX can be useful with certain modifications of treatment regimens and indications for non-transplant patients suffering from liver failure, pre-transplant patients, or for transplant patients having hepato-renal syndrome.

The activity as an adenosine $A_1$ receptor inhibitor and diuretic indicates that the subject antagonist compounds, e.g., ENX, also can be used as an analgesic, especially in the treatment of angina, claudication, and bradyarrhythmias associated with ischemia, hypoxia, or reperfusion. Also, the use of exogenously administered adenosine in cardiac diagnostic procedures, e.g., imaging of cardiac vasculature, is known to produce transitory side effects, including a brief onset of pain. As this side effect has been attributed to adenosine's binding to, and stimulation of, the $A_1$ receptor (but not the $A_2$ receptor), an adenosine antagonist inhibiting the binding of adenosine to that $A_1$ receptor can be used to counteract the pain experienced by a patient undergoing the procedure. The subject compounds, including ENX, selectively bind to the $A_1$ adenosine receptor, inhibiting the binding of adenosine (and thus blocking or counteracting any side effect associated with the binding of adenosine to the $A_1$ receptor).

Further, the subject antagonist compounds, including ENX, can be used as a bronchodilator, i.e., an antiasthmatic. ENX has been shown to relax tracheal smooth muscle, thus producing bronchodilation. This property is also common to other much weaker xanthine derivatives, e.g., theophylline. Such use of the subject antagonist compounds as an antiasthmatic treatment suggests that the compound can be useful when administered via an inhalation route.

Other routes of administration of the subject compounds can also be used. For example, it is generally contemplated to administer the compounds according to the optimal route indicated for the condition being treated. Thus, the compounds can be administered intravenously, per os, transdermally, etc., and in single or multiple dosage regimens, as would be understood by a person of ordinary skill in the art.

It would also be understood by ordinarily skilled artisans that the above-described uses for the subject compounds can be optimized by using particular isomers which demonstrate different biological activities. Having a chiral center, ENX is recognized to exist in at least two enantiomeric forms. The ENX enantiomers, namely, the S-enantiomer and the R-enantiomer, have been synthesized as the R- and S-isomers of 5-norbornene-2-carboxylic acid by methods available in the art. See Poll, T. et al. (1985) *Tetrahedron Lett.* 26:3095–3098, and Poll, T. et al. (1989) *Tetrahedron Lett.* 30:5595–5598. The endo-R-and endo-S-enantiomers of ENX are shown as Formulas IV and V, respectively.

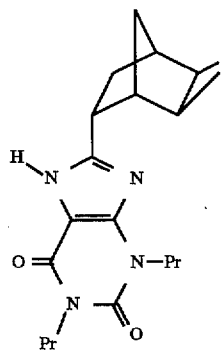

IV

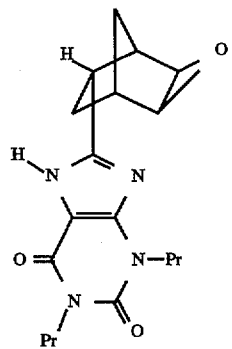

V

Studies conducted on the two enantiomers of ENX show that both are selective for the $A_1AR$ as compared to the $A_2AR$. The S-enantiomer has a longer duration of action than the R-enantiomer. Although a racemic mixture of the R- and S-enantiomers can have the biological activity of either or both isomers, it is now understood that the S- and R- isomers can be used separately, as a single enantiomer, to effect particular advantageous activities of either enantiomer.

For example, about 80–90% of the biological activity demonstrated by a racemic mixture of ENX is accounted for by the S-enantiomer. This result is primarily due to the very short duration of activity by the R-enantiomer as compared to the duration of action exhibited by the S-enantiomer. The prolonged action of the S-enantiomer can be due to a slower clearance rate in the liver, e.g., slower metabolic degradation by enzyme systems such as cytochrome $P_{450}$. The S-enantiomer, which showed slightly increased potency in vitro as compared to the R-enantiomer, showed substantially higher potency in vivo, and consequently higher selectivity for the $A_1$ adenosine receptor as compared to the $A_2$ receptor. See Example 4 for specific data comparing the selectivity and affinity properties of the S- and R-enantiomers of ENX.

The advantageous properties, e.g., increased potency (in vitro and in vivo) and higher selectivity, as well as the longer duration of action exhibited by the S-enantiomer, indicates that the S-enantiomer can be very useful as a diuretic in animals and humans. In most instances, as those exemplified above, the S-enantiomer can be the preferred compound because the length of its duration of activity, which is more than that of the R-enantiomer, can be critical to achieving its effect. In other words, the compound must at least cause an effect long enough to accomplish the desired result.

On the other hand, in instances where short duration of action are desired, e.g., during intravenous infusion of adenosine or onset of myocardial ischemia, when the onset of increased adenosine levels is rapid and lasts only for a short period of time (on the order of seconds or minutes), an adenosine antagonist having a short duration of action, e.g., the R-enantiomer of ENX, can be advantageously used. The activity of the ENX R-enantiomer is beneficial for short periods of time. However, the R-enantiomer of ENX is rapidly degraded or metabolized. This rapid metabolism can prevent complications associated with drug interactions because the concentrations of the ENX R-enantiomer are rapidly decreased. Due to its analgesic properties, the R-enantiomer of ENX can be administered for the acute pain of angina.

Another application of the subject compounds having a short duration of action is as an antiasthmatic or bronchodilator. It has been suggested that the high biological activity shown for the S-enantiomer of ENX is due to the rapid and selective metabolism of the R-enantiomer of ENX in the liver. This can be due to a first-pass effect exhibited for the R-enantiomer when administered by routes in which the drug is degraded by liver enzymes prior to or at about the same time as it reaches the appropriate receptors where the pharmacologic effect is induced. However, certain other routes of administration can be advantageously used to exploit this first-pass effect. For example, the S- and R-enantiomers of ENX have been demonstrated to be bronchodilators. Administration of the R-enantiomer alone (or in a composition comprising the R-enantiomer but not the S-enantiomer) by inhalation immediately presents the compound to the appropriate receptors in the trachea and bronchi to cause its action. Any absorbed compound is rapidly eliminated, which reduces residual levels of the compound in the body.

Derivatives of adenosine containing an epoxide moiety, particularly those having an epoxide moiety in an N-6 substituent, can be used as $A_1AR$ agonists. Epoxide derivatives of adenosine agonists can also display high selectivity for adenosine receptors. High selectivity for cardiac tissue is also demonstrated. More specifically, $N^6$-substitution of adenosine with epoxycycloalkyl groups can result in potent and tissue-selective agonists. Detailed structure activity and molecular modeling studies indicate that adenosine agonists interact with the $A_1$ receptor via three domains which accommodate $N^6$-, 2-, and 9- (ribose) substituents.

The $N^6$-subregion of the $A_1$ adenosine receptor contains chiral recognition sites which can be important for the determination of $A_1/A_2$ selectivity. The epoxide can be substituted as a cycloalkyl substituent, e.g., cyclopentyl, norbornanyl, or adamantanyl derivative of adenosine. Shown below as Formula VI is an adenosine epoxide having the epoxide substituent at the $N^6$ position. The epoxide can be attached as a cyclopentyl or norbornanyl group.

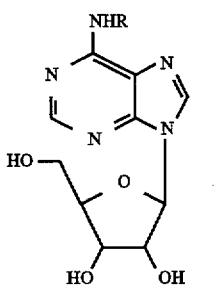

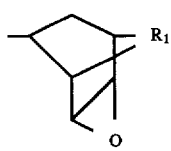

wherein R = or

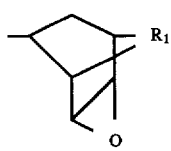

and $R_1$=an alkyl group of 1–4 carbons. Embodiments of the agonist compounds having an $N^6$-norbornyl group include the exo- and endo-isomers shown below as Formulas VII and VIII, respectively.

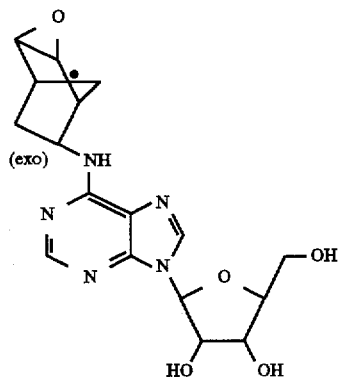

(VII)

(VIII)

The subject agonist compounds can be one of four isomers: the 2R-endo, 2R-exo, 2S-endo, or the 2S-exo form. The 2R-endo and 2S-endo enantiomers are shown as Formulae IX and X, below:

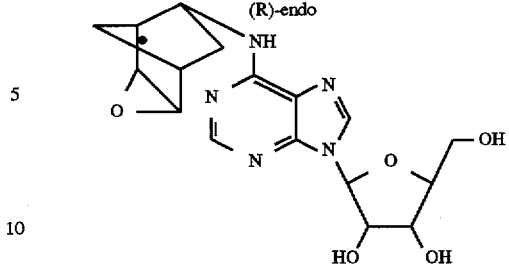

(IX)

(X)

Another embodiment of the subject agonist compounds includes the compound shown as Formula XI, below, which has an oxygen atom bonded at the N-1 position of the purine ring. This compound is termed $N^6$-(5,6-epoxynorborn-2-yl)adenosine-1-oxide.

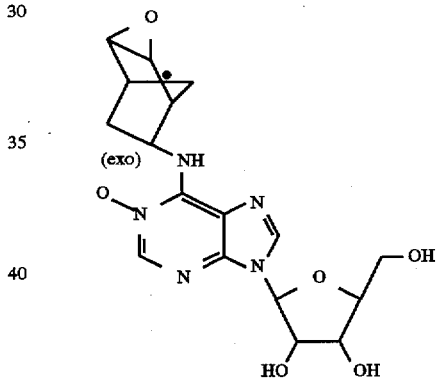

(XI)

Figure 2:
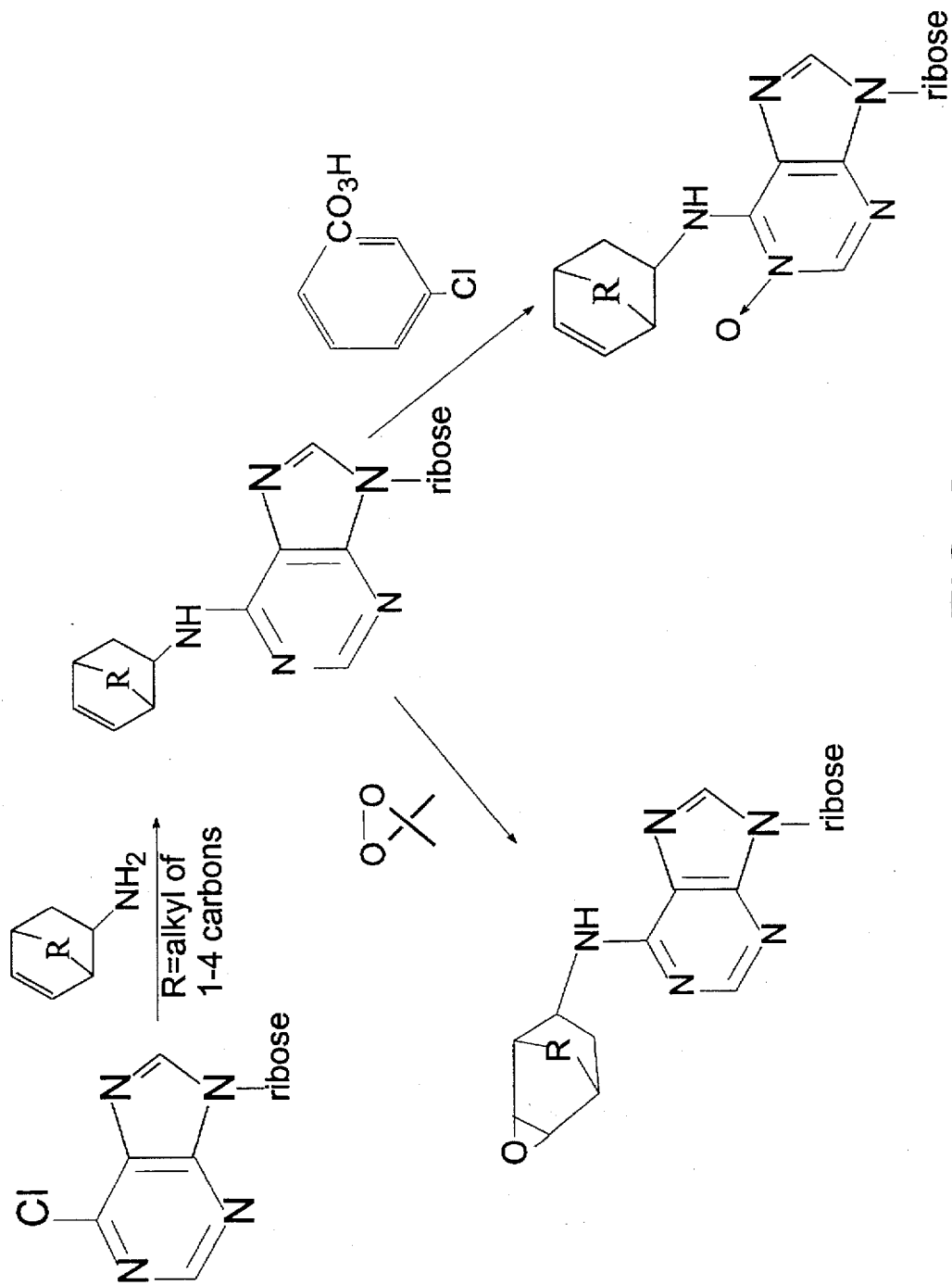
FIG. 2 shows a scheme (Scheme 1) using dimethyl dioxirane for the synthesis of an adenosine derivative having an epoxide moiety. Scheme 1 uses the specific exo- or endo-5-aminonorborn-2-ene to synthesize the respective exo- or endo-isomer of the resulting adenosine derivative. Also shown in FIG. 2 (Scheme 1 ) is the oxidation of a norbornene with an acid chloride (meta-chlorobenzoic acid) which is the accepted oxidation reaction, but results in oxidation at N-1 of the purine moiety.

As shown in FIG. 2, the exo-5-aminonorborn-2-ene was readily obtained in two steps from norbornadiene using procedures recognized in the literature. However, synthesis of the endo-isomer proved more difficult and was facilitated by use of norborn-2-carboxylic acid according to the method described herein and shown in FIG. 9A. Synthesis of the compound endo-5-aminonorborn-2-ene (compound 7b in FIG. 9A) from endo-norbornene-2-carboxylic acid has an advantage of being amenable to the synthesis of the 2R and 2S-endo isomers. The subject invention includes the discovery that trifluoroacetic acid (TFA) can be a useful reagent for converting intermediate isocyanates to trifluoroacetamides in a modified version of the Curtius reaction. TFA proved to be an efficient trapping reagent, and formation of the acyl azide from either an acid chloride (compound 9 in FIG. 9A, where X=Cl) or a mixed anhydride (compound 9 in FIG. 9A, where X=C(O)OEt) ultimately led to similar yields of the isomeric trifluoroacetamides (compound 11 in FIG. 9A), irrespective of whether the reaction was conducted in acetone or under phase transfer conditions (see Table 1). Despite similar polarity of the endo- and exo- isomers, a small quantity of the endo-isomer was successfully purified by column chromatography. Subsequent alkaline hydrolysis yielded the corresponding amine (compound 7b in FIG. 9B).

A more direct approach involved acid hydrolysis of the intermediate isocyanate in a carefully adjusted biphasic mixture. Thus, after refluxing the acyl azide/isocyanate in carbon tetrachloride with an equimolar amount of aqueous 2M HCl, conversion to the amine hydrochloride was achieved without affecting the norbornene double bond. This reaction proceeded in very high yield and is currently the most efficient synthesis of 5-aminonorborn-2-ene hydrochloride (compound 7c in FIG. 9B). In liberating 5-aminonorborn-2-ene from the hydrochloride salt, raising the pH and extracting with organic solvents gave low yields of the free amine. However, the hydrochloride salt could be used to directly alkylate 6-chloropurine riboside.

TABLE 1

Curtius rearrangement reaction conditions

| R—COOH→R—NCO (compounds 8→10) | Trapping/hydrolysis | Product | Yield (%) |
|---|---|---|---|
| (i) SOCL$_2$ | t-BuOH | — | — |
| (ii) NaN$_3$, Δ | | | |
| (i) SOCl$_2$ | TFA | 11 | 56 |
| (ii) NaN$_3$, H$_2$O (NBu$_4$Br, CCl$_4$) | | | |
| (i) ClC(O)OEt, NEt$_3$ (acetone) | TFA | 11 | 57 |
| (ii) NaN$_3$, H$_2$O | | | |
| (i) SOCl$_2$ | TFA | 11 | 57 |
| (ii) NaN$_3$, H$_2$O (acetone) | | | |
| (i) SOCl$_2$ | 2N HCl | 7c | 96 |
| (ii) NaN$_3$, H$_2$O (NBu$_4$Br, CCl$_4$) | | | |
| (i) ClC(O)OEt, NEt$_3$ (acetone) | 2N HCl | 7c | 94 |
| (ii) NaN$_3$, H$_2$O | | | |

6-chloropurine riboside reacted with exo- and endo-5-aminonorborn-2-ene (compounds 7a and 7b in FIG. 9A, respectively) to yield the $N^6$-substituted adenosines, $N^6$-(endo-norborn-5-en-2-yl) adenosine or $N^6$-(exo-norborn-5-en-2-yl) adenosine. The final step, conversion of these alkenes to epoxides, was carried out by treating $N^6$-(norborn-5-en-2-yl) adenosine with m-chloroperbenzoic acid in dichloromethane. After the addition of 1 molar equivalent of peracid, two compounds were observed by t.l.c. Addition of m-chloroperbenzoic acid (a further 2 equivalents) was continued until only the compound was observed. Purification was achieved via column chromatography using a mixture of ethyl acetate, chloroform, and ammonia (85:15:1) as an eluent. Replacement of the olefinic signals at δ6.17 and 6.20 by a 2-proton singlet at δ3.23 in the $^1$H NMR spectrum was consistent with oxidation of the alkene moiety. However, the mass spectrum showed a molecular ion at 392 (16 mass units higher than expected), suggesting that oxidation also occurred at N1. Repeating the reaction with less peracid and close monitoring by t.l.c. and NMR, small portions of approximately 0.1 equivalent were added over a 48-hour period. The formation of N-oxide was detected immediately, and, after all of the starting material was exhausted, a 1.5:1 ratio of N-oxide:$N^6$-(endo/exo-norborn-5-en-2-yl) adenosine was observed by NMR. Oxidation N1 was avoided by use of dimethyldioxirane which selectively epoxidized to the alkene and afforded $N^6$-(endo/exo-epoxynorborn-5-en-2-yl) adenosine in high yield. The volatile nature of the principal byproduct (acetone) greatly facilitated the isolation of the product and obviated extensive chromatography. Dimethyldioxirane is a preferred oxidant due to it selectivity for the alkene moiety and the ease of purification of the oxidized product and can be employed for the conversion of the exo-, endo-, or racemic norbornene to the respective exo-, endo-, or racemic epoxide. Other oxidants selective for the alkene moiety as recognized in the art can also be employed.

Biological activity can also be enhanced by modifying other parts of the cycloalkyladenosine molecule. For example, both 2- and 5'-chloro substitutions of $N^6$-cycloalkyladenosines have been used to increase $A_1$ selectivity. FIG. 2 shows one example of a scheme for chemically converting an adenosine molecule or its derivative to an adenosine compound comprising an epoxybicycloalkyl group as an $N^6$ substituent. Preferably, dimethyldioxirane is the oxidant used in the formation of the epoxide of the adenosine compound. See Iyer, R. S. et al. (1994) *J. Am. Chem. Soc.* 116:1603–1609. The dimethyldioxirane can be made according to methods and procedures known in the art. See Murray, R. W., R. Jeyaraman (1985) *J. Org. Chem.* 50:2847–2853; Adam, W. et al. (1991) *Chem. Ber.* 124:2377.

The subject adenosine agonists can be useful for the treatment of a patient where stimulation of $A_1AR$ is needed. Uses for the subject adenosine agonists and compositions comprising those agonists include their use as a functional β-blocker; as an antiarrhythmic agent for the control of heart rate, including supraventricular tachyarrhythmias, catecholamine (cAMP-dependent) supra- and ventricular-arrhythmias; diabetes type II; and cardioprotection, e.g., decrease infarct size and increase tolerance to myocardial ischemia.

In particular, the subject agonist compounds can be useful in the treatment of adenosine-sensitive supraventricular tachyarrhythmias, e.g., for ventricular rate control in atrial flutter or in atrial fibrillation, or in the inhibition of A—V nodal transmission in supraventricular tachycardia, by administering an effective amount of the agonist to a patient in need of such treatment. In a preferred embodiment, the endo-5,6-epoxynorborn-2-ene adenosines are used in such treatments by administering an effective amount of the compound to the patient. The compound can be administered as a racemic mixture of the 2R- and 2S enantiomers or can be administered as either the 2R- or 2S-enantiomer. A more preferred embodiment is the endo- form of the 2R-, 2S, or 2R-/2S- racemic mixture. A most preferred embodiment is the 2S-endo- form of the subject agonist, which is termed $N^6$-(2S-endo-5,6-epoxynorborn-2-yl) adenosine, shown as Formula X. This particular enantiomer has been demonstrated to have more than 100-fold higher potency for slowing of A—V ($A_1$ effect) conduction than for coronary vasodilation ($A_2$ effect) with no discernable hypotensive ($A_2$) effect in whole animals.

It would also be understood by a person of ordinary skill in this art that the ribose moiety of the agonist compounds can be modified, which can provide certain advantages. For example, it is well known that the ribose moiety can be acetylated, chlorinated, or methylated, whereby such modification can improve solubility or absorption or prolonged half-life of the molecule. Preferably, such modification occurs at the hydroxyl attached to the C-5 of the ribose molecule. These, or other similar substitutions of the hydroxyl substituents on the ribose moiety, including deoxy-forms of the agonist compounds, can also be prepared by ordinarily skilled artisans and used as described herein and are considered to be part of the subject invention.

The subject compounds can provide a method for normalization of ventricular rhythm and improve ventricular hemodynamics or cardiac output in atrial fibrillation. Administering a compound of the subject invention to a patient in atrial fibrillation is a unique method for pharmacologically achieving normal ventricular rhythm, thereby improving ventricular hemodynamics and cardiac output in a patient in atrial fibrillation.

The compounds of the subject invention (agonists and antagonists) can be formulated with a pharmaceutically acceptable carrier into a composition that can be administered to a patient who would benefit from the adenosine receptor agonist or antagonist properties of the subject compounds or compositions.

Advantageously, dosages of the subject adenosine antagonists for treating post-resuscitation cardiac arrhythmias can be less than the 0.1–20 mg/kg range which has been previously reported for known adenosine antagonists. See U.S. Pat. No. 4,980,379. An effective dose can be recognized as the dose at which the alleviation of bradycardia and reversal of hemodynamic collapse occurs.

Standard procedures for administration of adenosine antagonists such as theophylline and aminophylline at effective dosage levels are well established and are well known to those skilled in the art. For example, the recommended therapeutic range for plasma levels of theophylline for patients with reversible obstruction of the airways is from 10–20 µg/ml. The subject compounds, having high selectivity and potency, can be useful and effective at known concentrations in the blood.

The above list of treatment uses for the subject compounds or compositions is by no means exhaustive, and other situations where the subject invention could be advantageously employed would be readily recognized by ordinarily skilled persons in this art. For example, it would be readily recognized in the art that other conditions which can be treated by reducing the effects of elevated endogenous adenosine or by increasing stimulation of the $A_1AR$ can also benefit from the use or administration of the subject adenosine antagonists or agonists, respectively.

Following are examples which illustrate procedures, including the best mode, for practicing the invention. These examples should not be construed as limiting. All percentages are by weight and all solvent mixture proportions are by volume unless otherwise noted.

EXAMPLE 1
Preparation of 8-Epoxyalkylxanthines

Chemistry. The scheme shown in FIG. 1 outlines the syntheses of 1,3-dipropylxanthines having C-8 substituents comprising an epoxide moiety. The reaction of 5,6-diamino-1,3-dipropyluracil, 1, with an ω-alkenoyl halide or an ω-alkenoyl ester gave an amide 2, which was then cyclized in hot alkali to form the 8-ω-alkenyl-1,3-dipropylxanthine 3. Oxidation with m-chloroperbenzoic acid yielded the 8-epoxyalkylxanthine 4. Alternatively, the Diels-Alder condensation of 3 with a 1,3-cycloalkadiene generated an 8-bicycloalkenylxanthine 5. When furan was the alkadiene the product was the 8-ω-{7-oxabicyclo[2.2.1]hept-2-en-5(6)-yl}xanthine 5, which contains both (a) an epoxide moiety and (b) an alkenyl moiety that can serve for the formation of a second epoxide moiety. The oxidation of 5 with 2.4 equivalents of meta-chloroperbenzoic acid gave the 8-epoxybicycloalkylxanthine 6.

1,3-dipropyl-8-{3-oxatricyclo[3.2.1.0$^{2,4}$]oct-6(7) yl}xanthine. A solution of 8bicyclo[2.2.1]hept-2-en-5(6) ylxanthine (1.0 g, 3 mmol) and m-chloroperbenzoic acid (0.8 g, 3.6 mmol) in 50 ml $CH_2Cl_2$ was stirred for 24 hours at room temperature. A second aliquot of peracid was added and stirring continued for 24 hours. Evaporation gave a yellow oil that was purified by preparative reverse phase HPLC on C-18 silica eluted with a gradient of 70–80% methanol in water. Yield 0.54 g, 52%, mp 149°–150° C.

1,3-dipropyl-8-{7-oxabicyclo[2.2.1]hept-2-en-5(6)yl} xanthine. A suspension of 1,3-dipropyl-8-vinylxanthine (0.4 g, 1.5 mmol) in 50 ml dry THF containing furan (0.22 ml, 3 mmol) was stirred at room temperature. The addition of 1 drop of TMS triflate effected solution, and HPLC showed the disappearance of starting material. Preparative reverse phase HPLC on C-18 silica eluted with a gradient of 50–80% methanol in water yielded 0.25 g (50%) of product.

EXAMPLE 2
Preparation of an Adenosine Derivative Comprising an Epoxide Moiety.

A compound useful as an adenosine agonist is an adenosine derivative comprising an oxabicyclo- or oxatricycloalkyl group as an N-6 substituent. A general scheme for the preparation of the compound is shown in FIG. 2.

$N^6$-endo-{3-oxatricyclo[3.2.1.0$^{2,4}$]oct-6(7)-yl }adenosine. A solution of $N^6$-(endo-2-norbornene-5-yl) adenosine (0.5 g, 1.4 mmol) in 100 mL dry methanol was cooled to 0°–5° C. in an ice bath, a solution of dimethyldioxirane in acetone (40 mL, 4 mmol) was added; stirring continued for 8 hours in the ice bath and then overnight at room temperature. Evaporation of solvent and purification by chromatography yielded 0.42 g (81%) of a white solid.

EXAMPLE 3
Use of the Novel Compounds as Adenosine Antagonists

In order to demonstrate the effectiveness of the subject compounds as adenosine antagonists, the activity of the compounds was compared to known antagonists. In addition, the specificity, selectivity, and potency of ENX as an $A_1$ adenosine receptor antagonist, functional and biochemical (radioligand binding assays) experiments were carried out on guinea pig isolated hearts, in membranes from guinea pig brain, $DDT_1MF-2$, and PC12 cells. The results of these experiments are described below.

1. Functional studies. The functional evidence that an epoxide of alkylxanthine (ENX) specifically and selectively antagonizes cardiac actions of adenosine mediated by $A_1$-adenosine receptor but does not antagonize $A_2$-adenosine-receptor mediated coronary vasodilation was obtained in the isolated perfused guinea pig heart. The effect of ENX and two other alkylxanthines (NAX and CPX) on the $A_1$receptor mediated changes in stimulus-to-His bundle interval (S—H interval; a measure of AV nodal conduction) and on the $A_2$ receptor mediated coronary vasodilatation were investigated. The potency of ENX, NAX, and CPX to antagonize the negative dromotropic (prolongation of S—H interval) of the $A_1$ agonist CCPA and vasodilatory effect of adenosine are shown in Tables 2 and 3.

TABLE 2

Potency of various alkylxanthines to antagonize $A_1$ receptor-mediated cardiac response: results of Schild analysis.

|  | ENX | NAX | CPX |
|---|---|---|---|
| $PA_2$ | 8.45 ± 0.19 | 8.79 ± 0.15 | 8.76 ± 0.02 |
| $K_B$ | 3.6 nM | 1.6 nM | 1.7 nM |
|  | (1.2–3.9) | (1.1–3.2) | (1.6–1.9) |
| Slope | −0.91 ± 0.06 | −0.89 ± 0.11 | −0.81 ± 0.03 |
| n | 4 | 3 | 3 |

Values are mean ± S.E.M. of the $PA_2$ (−log$_{10}K_B$), the equilibrium dissociation constant $K_B$, and the slope of Schild plot. Cardiac response: antagonism of the negative dromotropic effect of the selective $A_1$ agonist CCPA. The numbers in parentheses are the minimum and maximum $K_B$ values.
n = number of experiments.
Neither the $PA_2$ ($K_B$) nor the slope of Schild plots were significantly different among the antagonists.

TABLE 3

Potency of various alkylxanthines to antagonize $A_2$ receptor-mediated coronary vasodilation.

|  | ENX | NAX | CPX |
|---|---|---|---|
| $IC_{50}$ | no effect (0% at 50 μM) | 7.1 μM (4.8–9.4) | 1.5 μM (0.8–2.2) |
| n | 4 | 3 | 3 |

Values are the concentration of antagonist that inhibits 50% ($IC_{50}$) of a maximum coronary vasodilation caused by adenosine. Values in parentheses are 95% confidence interval of the $IC_{50}$ values. n = number of experiments.

Although all three alkylxanthines were equipotent in antagonizing the $A_1$-receptor mediated prolongation of the S—H interval, ENX is far more selective than NAX and CPX.

To further demonstrate the selectivity of ENX for $A_1$ vs $A_2$ receptor, measurements of $A_1$-receptor mediated S—H interval and $A_2$-receptor mediated increase in coronary conductance were carried out during administration of adenosine alone and adenosine plus ENX (FIGS. 4A–4D). Adenosine (Ado, 4 μM), when administered alone, produced a significant increase in S—H interval and coronary conductance. When adenosine was administered together with ENX (0.4 μM), the S—H interval prolongation was completely inhibited, whereas the $A_2$-mediated coronary vasodilation remained unaltered. After washout of ENX, a third administration of adenosine alone caused a significant prolongation of S—H interval (similar to the first administration of adenosine) and increase in coronary conductance. These findings demonstrate that the effects of ENX are reversible and that ENX antagonizes the $A_1$-receptor mediated S—H prolongation but not the $A_2$-receptor mediated increase in coronary conductance caused by adenosine. These data also demonstrate the capability of ENX to inhibit activity (and thus any side effects) associated with the binding of adenosine to the $A_1$ receptor while the beneficial pharmacological activity of adenosine stimulation of the $A_2$ receptor remains unaffected.

To determine whether ENX had a positive inotropic effect, experiments were conducted to determine its effects on left ventricular pressure (LVP) and its first derivative dP/dt, an index of contractility. As illustrated in FIG. 5, there were no significant changes in either LVP or dP/dt of normoxic guinea pig hearts when these hearts were exposed to increasing concentrations of ENX (2–200 μM). LVP and dP/dt remained constant during the administration of varying concentrations of ENX and washout. These results demonstrate the lack of a positive inotropic effect of ENX.

Figure 6:
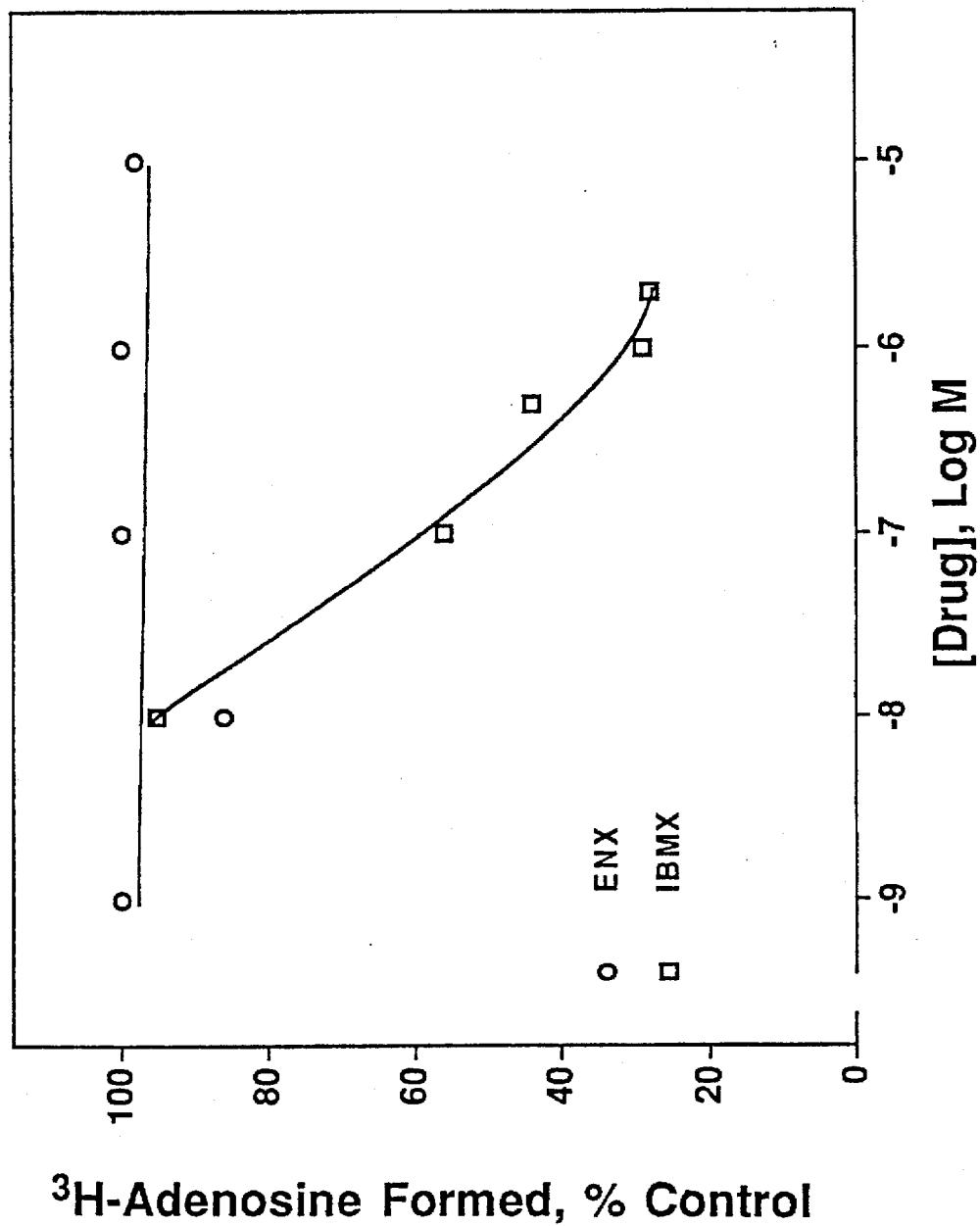
FIG. 6 shows the effect of ENX and isobutylmethylxanthines (IBMX) on phosphodiesterase (PDE) activity in homogenates of DDT$_1$MF-2 cells. The data for IBMX, shown as squares in the figure, clearly shows inhibition of phosphodiesterase activity. In contrast, phosphodiesterase activity following ENX administration, shown as circles in the figure, remained constant and showed no inhibition.

Consistent with the lack of positive inotropic effect, ENX also did not inhibit the enzyme phosphodiesterase (FIG. 6). Cells were homogenized in 40 mM Tris buffer at pH 8.0, and the whole homogenate was used in the enzyme assays. PDE activity was determined by incubating homogenate (0.4 mg protein) in Tris buffer containing 20 mM $MgCl_2$, 4 mM mercaptoethanol, 0.06 mg bovine serum albumin, 0.4 mM cAMP 130 nCi of [$^3$H]cAMP and the indicated concentrations of ENX or IBMX for 45 min at 30° C. Blank incubations were carried out in parallel assays without the homogenate. At the end of the incubation, the suspensions were incubated in a boiling water bath for 2 minutes, transferred to an ice-water bath for 2 minutes and 0.1 mg of snake venom phosphodiesterase was added. The suspensions were incubated for 10 minutes at 30° C., and the adenosine formed was isolated by ion exchange chromatography. The control rate of adenosine formed was 220 pmol/mg protein per minute. The amount of adenosine formed was linear over the incubation period used.

Agents that inhibit the enzyme phosphodiesterase are known to produce positive inotropic effect. The results illustrated in FIG. 6 clearly showed that ENX does not inhibit phosphodiesterase, whereas isobutylmethylxanthine (IBMX, a known positive inotropic agent) inhibits phosphodiesterase. These findings demonstrate an advantage of ENX over other alkylxanthines that are known to inhibit phosphodiesterase, and therefore have the potential to produce a positive inotropic action.

Figure 7:
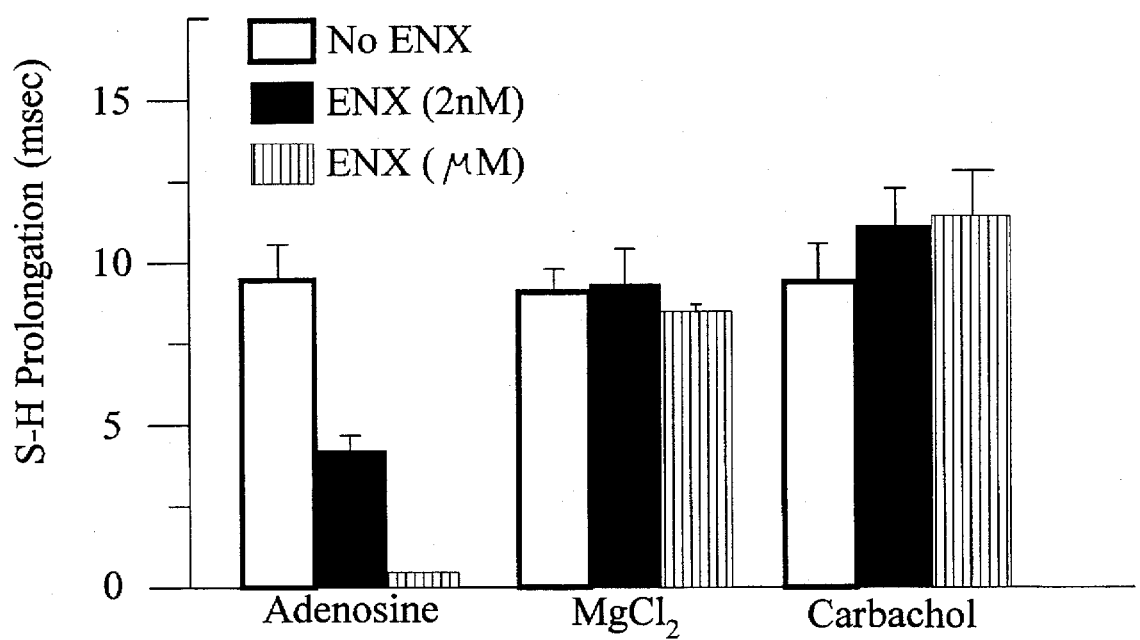
FIG. 7 shows the specificity of action of ENX to antagonize the negative dromotropic effect (S—H prolongation) of adenosine in guinea pig heart. The effect of ENX (2 nM, 2 µM) on similar S—H prolongation caused by adenosine (ADO, 4 µM), magnesium (Mg$^{2+}$, 3 mM), and carbachol (CCh 0.14 µM) was determined. The height of each bar graph presents the mean±SEM of 4 experiments. Only the S—H interval prolongation caused by adenosine was antagonized by ENX.

Carbachol and $MgCl_2$ were used to test the specificity of antagonism by ENX, e.g., S—H interval prolongation mediated by adenosine As illustrated in FIG. 7, ENX (2 nM, 2 μM) did not antagonize the negative dromotropic effect of carbachol or $MgCl_2$. In contrast, ENX did antagonize the S—H prolongation caused by adenosine.

In summary, the results of the functional experiments described above demonstrate that in the heart, ENX is a reversible, specific, and highly selective antagonist of adenosine at the $A_1$ receptor subtype.

2. Radioligand binding studies. To determine the binding affinities of an epoxide of alkylxanthine, ENX, and compare to other alkylxanthines (CPX, NAX and CPT), radioligand binding experiments were carried out in membranes prepared from brain tissue, $DDT_1MF-2$ and PC12 cell lines. The results of these experiments are illustrated in Tables 4 and 5. The results summarized in Table 4, below, indicate that in brain tissue, ENX is more potent than the other alkylxanthines at the $A_1AR$, whereas in $DDT_1MF-2$ cell the binding affinity of the alkylxanthines for the $A_1$ receptor are approximately the same. With regard to $A_2$ receptors in PC12 cell membranes, ENX was markedly less potent than CPX. In addition, the binding affinity of ENX for the $A_1$ receptor, either brain or $DDT_1MF-2$ cells, was markedly higher than that at the $A_2$ receptor in PC-12 cell membranes.

TABLE 4

Binding affinities of alkylxanthines for the $A_1$- and $A_2$-adenosine receptors in brain, $DDT_1$-$MF_2$ and PC-12 cell membranes

| | $K_i$ (nM) | | |
|---|---|---|---|
| Alkylxanthine | Brain | $DDT_1MF_2$ | PC-12 |
| ENX | 0.45 ± 0.22 (5) | 0.22 ± 0.03 (5) | 11,666 ± 366 (4) |
| CPX | 4.4 ± 0.8 (4) | 0.13 ± 0.01 (4) | 320 ± 40 (3) |
| NAX | 3.8 ± 0.21 (4) | 0.18 ± 0.05 (3) | — |
| CPT | 41.0 ± 13.0 (4) | — | — |

$A_1$ receptor binding was carried out with [$^3$H]CPX in guinea pig forebrain and cardiac membranes, and in intact $DDT_1$-$MF_2$ cells. $A_2$ receptor binding was carried out with [$^3$H]NECA in PC-12 cell membranes. Values are mean ± SEM of triplicate determinations in each of several (n) preparations. $K_i$ values were calculated as described in methods. Abbreviations for the alkylxanthines are as follows:
ENX = 1,3-dipropyl-8-{3-oxatricyclo[3.1.2.0$^{2,4}$] oct-6(7)-yl}xanthine;
CPX = 8-cyclopentyl-1,3-dipropylxanthine;
NAX = 1,3-dipropyl-8-(3-noradamantyl)xanthine; and
CPT = 8-cyclopentyl-1,3-dimethylxanthine.

Additional radioligand binding studies have been carried out in guinea pig forebrain ($A_1$ receptor) and striatum ($A_2$ receptor) to demonstrate the greater $A_1$ receptor selectivity of ENX as compared to the previously known adenosine receptor antagonists, NAX or CPX. Table 5 shows $A_1$ and $A_2$ receptor binding affinities of brain tissue expressing $A_1$ (forebrain) and $A_2$ (striatum) adenosine receptors. The results of Table 5 clearly illustrate that ENX is significantly more selective for $A_1$ than $A_2$ receptors than the other alkylxanthines, NAX and CPX. That is, ENX was 800-fold selective for $A_1$ vs. $A_2$, whereas NAX and CPX were only 20 and 7.5 fold selective for $A_1$ vs. $A_2$, respectively. These results of these radioligand binding studies are fully consistent with that of the functional studies in guinea pig isolated hearts.

TABLE 5

Binding affinities of alkylxanthines for the $A_1$ and $A_2$ adenosine receptor in brain membranes

| Alkylxanthine | $K_i$ (nM) | | Ratio $A_1/A_2$ |
| --- | --- | --- | --- |
| | $A_1$ (forebrain) | $A_2$ (striatum) | |
| ENX | 0.45 ± 0.13 | 360 ± 36 | 800 |
| NAX | 1.10 ± 0.15 | 22 ± 6.90 | 20 |
| CPX | 8.4 ± 3.00 | 63 ± 5.40 | 7.5 |

$A_1$ and $A_2$ receptor binding was carried out with [$^3$H]CPX and [$^3$H]CGS 21,860 in guinea pig forebrain and striatum, respectively. Values are mean ± S.E.M. of triplicate determinations in each of four preparations.

EXAMPLE 4
Activities of ENX Enantiomers

The S-enantiomer and R-enantiomer of ENX were synthesized, as described, and tested for their relative activities and potencies. As shown in Table 6, below, the lower dissociation constant of the S-enantiomer of ENX suggests slightly higher potency ($K_i$=0.98) as compared to the R-enantiomer ($K_i$=2.1).

TABLE 6

Equilibrium dissociation constants of ENX enantiomers and CPX for rat brain $A_1$ adenosine receptors.

| Compound | $K_d$ or $K_j$, nM |
| --- | --- |
| [$^3$H]CPX | 0.49 |
| R-ENX | 2.1 |
| S-ENX | 0.98 |

In addition, the S-enantiomer of ENX demonstrated higher binding selectivity for the $A_1$ receptor. See Table 7, below.

TABLE 7

Potency and selectivity of ENX to antagonize radioligand binding to rat brain adenosine $A_1$ and $A_2$ receptors ("IC$_{50}$"* values)

| | $A_1$ | $A_2$ | Selectivity |
| --- | --- | --- | --- |
| ENX (racemate) | 1.65 nM | 2.1 µM | 1300 |
| S-ENX | 1.15 nM | 9.0 µM | 7800 |
| R-ENX | 2.70 nM | 2.6 µM | 960 |

*"IC$_{50}$" refers to the concentration at which radioligand binding to receptors was 50% inhibited.

Figure 8:
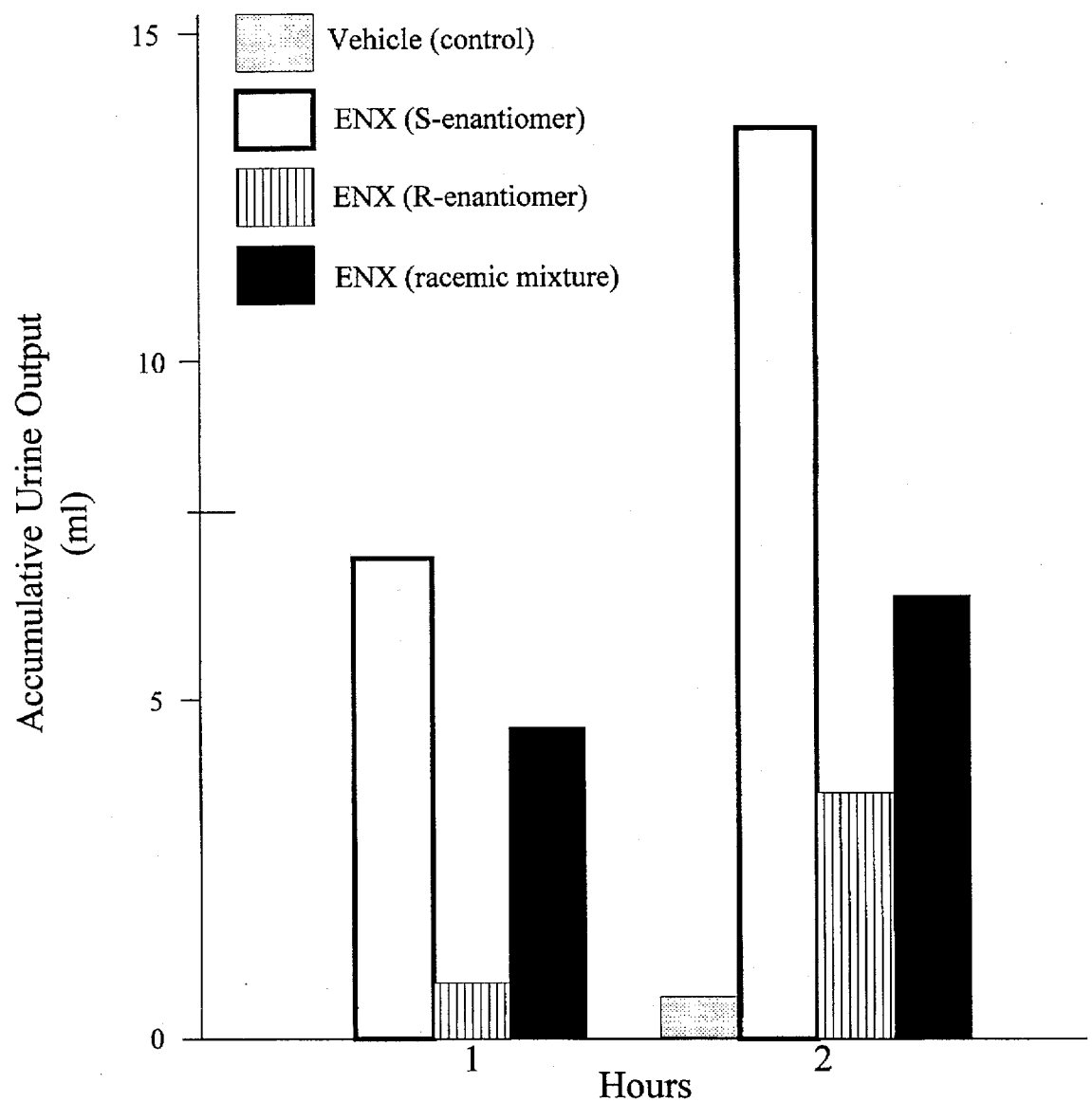
FIG. 8 shows accumulative urine output in rats intravenously given 0.1 mg/kg of ENX (racemic) mixture; ENX (R-enantiomer); ENX (S-enantiomer); and a vehicle used as a control.

The increased potency of the S-enantiomer is shown in FIG. 8. As shown, most of the diuretic activity exhibited by ENX as a racemic mixture resided in the S-enantiomer. Specifically, FIG. 8 shows a cumulative urine output measured for a period of 2 hours in rats administered 0.1 mg/kg ENX racemate, ENX R-enantiomer, and ENX S-enantiomer. It is therefore shown that, as a diuretic, the S-enantiomer of ENX is more potent than the R-enantiomer of ENX or a racemic mixture of R-and S-enantiomers of ENX. The duration of action is also longer for the S-enantiomer of ENX. These properties of the ENX S-enantiomer suggest its preferable use as a long-lasting diuretic in treating conditions normally calling for administration of a diuretic. Standard pharmacologic screening tests showed that the S-enantiomer of ENX (100 mg/kg per os) relaxed constricted guinea pig tracheal muscle. The S-enantiomer of ENX reduced serum cholesterol and heparin precipitating β-lipoproteins in mice after 100 mg/kg per os. Of interest, the observed reduction in HPL/CHOL ratio below 0.92 suggests a possible decrease in atherogenic low density β-lipoproteins.

Saluretic activity associated with increased urine volume output was observed in the hydrated rat at doses of and above 3 mg/kg per os. Moderate kaluretic activity was also noted after 30 mg/kg per os in this preparation, suggesting potassium sparing diuretic activity.

The R-enantiomer was shown to have activity as an antagonist of adenosine. Specifically, the R-enantiomer was observed to induce relaxation of spontaneous tone in guinea pig trachea. Saluretic activity associated with increased urine volume output was observed in the hydrated rat at 10 mg/kg per os of the ENX R-enantiomer. However, the activity of the ENX R-enantiomer has a very short duration of action as compared to the S-enantiomer. However, that can be useful in treating conditions that indicate short-acting treatments.

EXAMPLE 5
Synthesis of $N^6$-Substituted Adenosine Derivatives

The subject agonist compounds shown as Formula VI can be synthesized according to known procedures. For example, a general synthesis scheme for obtaining these compounds initially involves alkylation of an appropriately substituted amine, e.g., a bicyclic amine, with 6-chloropurine riboside. This straightforward reaction has been commonly used for the synthesis of $N^6$-substituted adenosines. See WO 84 04 882 (1985).

The substituted amine can be functionalized with a double bond which can then be oxidized to generate the epoxide product. m-Chloroperbenzoic acid can be used for this oxidation reaction. See also Sharpless, K. B., W. Amberg, Y. L. Bennani, G. A. Crispino, J. Hartung, K. -S. Jeong, H. -L. Kwong, K. Morikawa, Z. -M. Wong, D. Xu, X. -L. Zhang (1992) J. Org. Chem. 57:2768–2771; and Kolb, H. C., B. K. Sharpless (1992) Tetrahedron 48:1015–1030.

An alternative method of generating epoxides is the osmium-catalyzed dihydroxylation of olefins, which is now well known in view of the discovery of phthalazine ligands and that osmate ester hydrolysis is acceleration by organic sulfomamides. A simple, one-pot procedure for the conversion of vicinal diols into epoxides is known in the art (Kolb, H. C., B. K. Sharpless, supra). This reaction proceeds without epimerization via halohydrin ester intermediates. Combination of these methods allows epoxides to be obtained from olefins in a stereospecific fashion.

The substituted amines which can be used for synthesis of the subject compounds shown as Formulae VI–XI are 3-cyclopenten-1-yl amine (for the cyclopentene oxide derivative of adenosine) or 5-norbornen-2-yl amine (for the cyclohexene epoxide derivative of adenosine). 3-Cyclopenten-1-yl-amine can be synthesized from c/s-1,4-dichlorobutene and diethyl malonate via a 5-step reaction sequence which is known in the art (Murdock, K. C., R. B. Angier [1962] J. Org. Chem. 27:2395–2398).

The synthesis of 5-norbornene-2-yl amine can proceed from 5-norbornene-2-carboxylic acid, commercially available as a mixture of four isomers, 2R and 2S, each endo and exo. Conversion of this carboxylic acid to acyl chloride, followed by treatment with sodium azide, yields an acyl azide. Curtius rearrangement (loss of $N_2$ and migration of the substituent group) and subsequent hydrolysis yields 5-norbornen-2-yl amine as a mixture of isomers. This reaction sequence can be performed as a continuous operation without the isolation of the acyl azide or isocyanate in the synthesis of 4-aminocyclohexene. Another variation used for the Curtius rearrangement involves the preparation of the acyl azide by treatment of the corresponding acyl hydrazine with nitrous acid. In both cases, the rearrangement retains the absolute configuration at the chiral center. The endo and exo components can be separated by HPLC methods known in the art.

Figure 3:
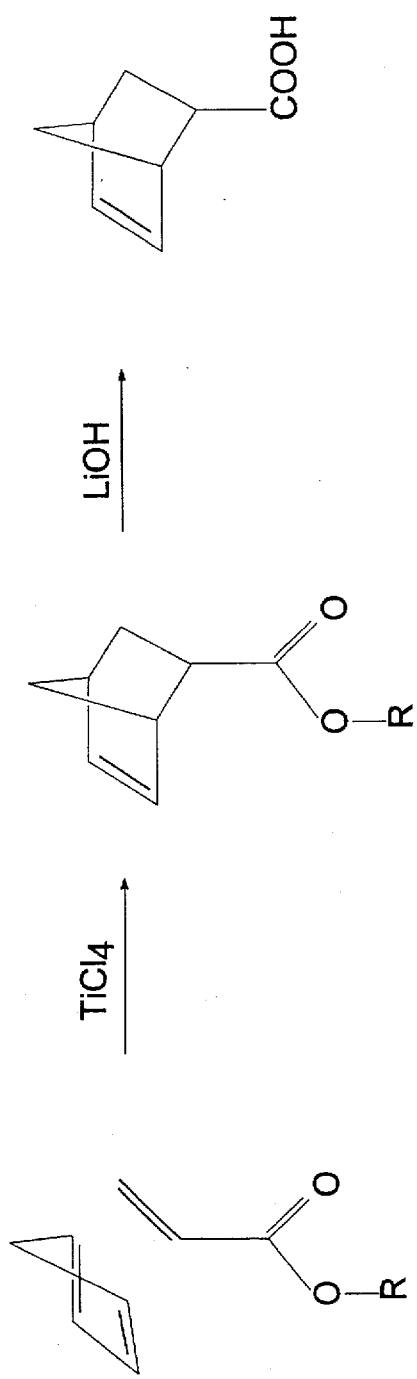
FIG. 3 shows synthesis of (2R)- and (2S)- and (2S)-endo-5-norbornen-2-carboxylic acids.
Figure 3:
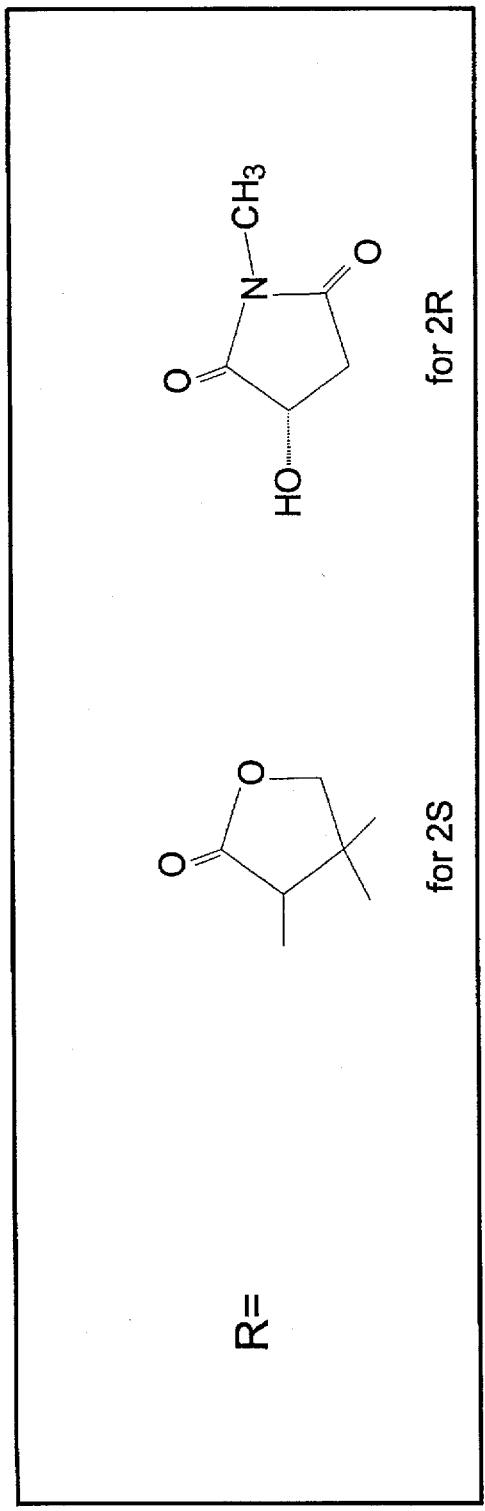
Figure 4A:
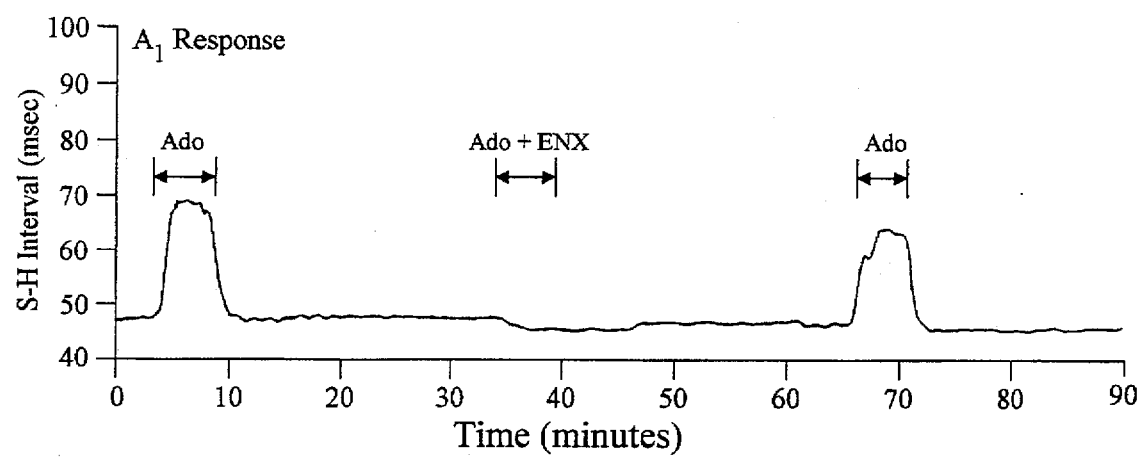
FIGS. 4A–4D show selective antagonism of the negative dromotropic (S—H interval prolongation) effect of adenosine (Ado) by ENX.
Figure 4B:
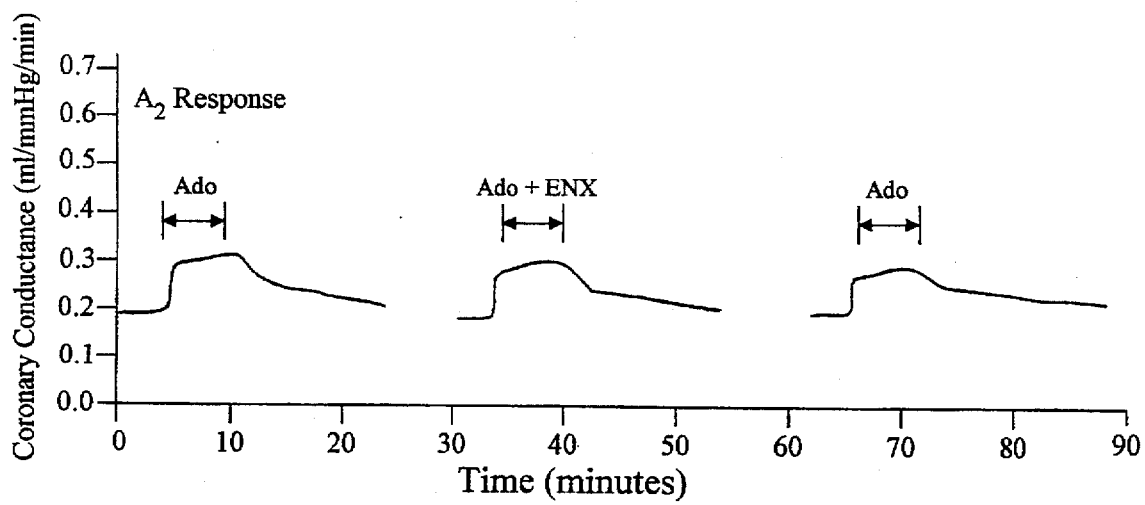
Figure 4C:
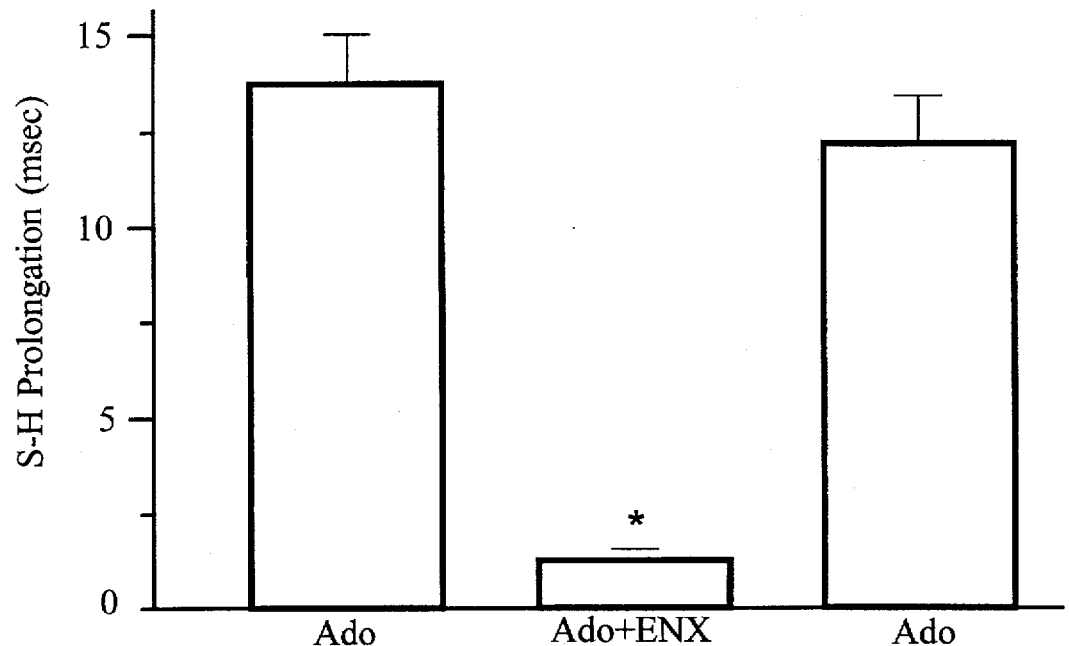
Figure 4D:
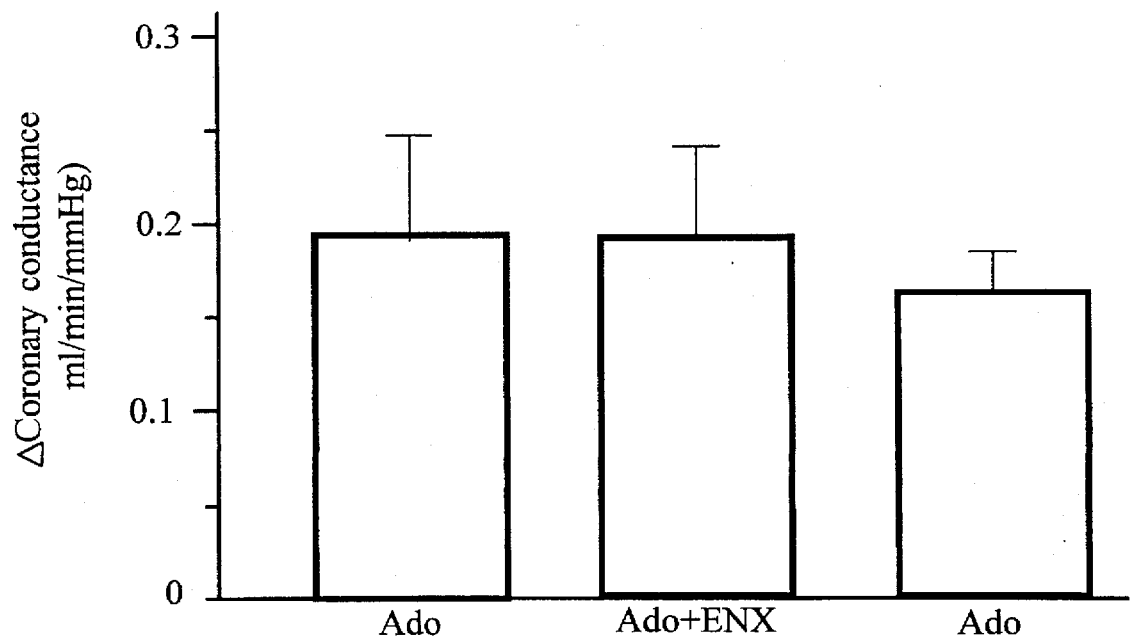
Figure 5A:
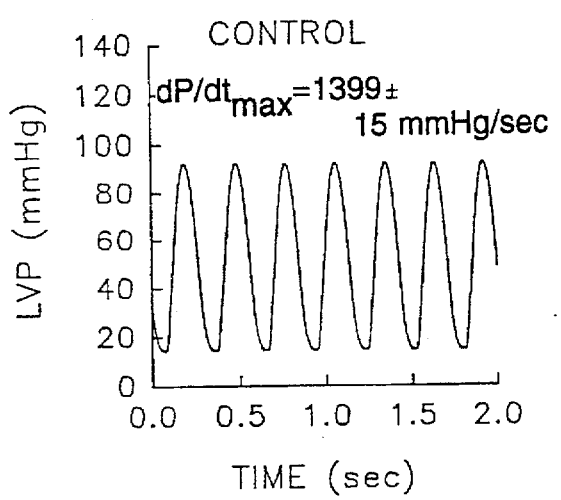
FIGS. 5A–5D show a lack of effect of ENX on left ventricular pressure (LVP) and dP/dt$_{max}$. Guinea pig hearts were atrial paced at a constant cycle length of 300 msec and exposed to progressively higher concentrations of ENX, i.e., 2 and 200 µM. In the same hearts ENX alone caused no significant changes in the stimulus-to-His bundle interval (not shown). Identical results were obtained in three other hearts.
Figure 5B:
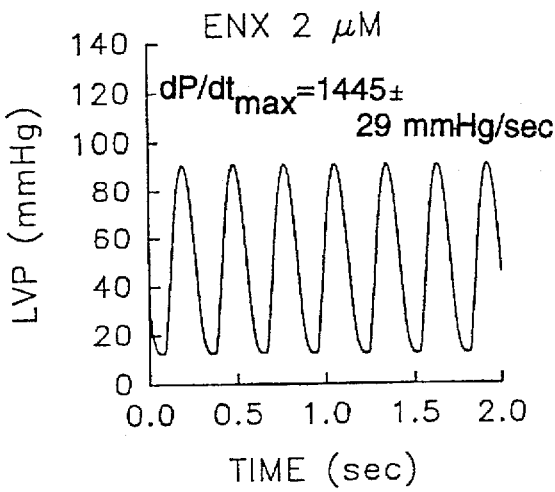
Figure 5C:
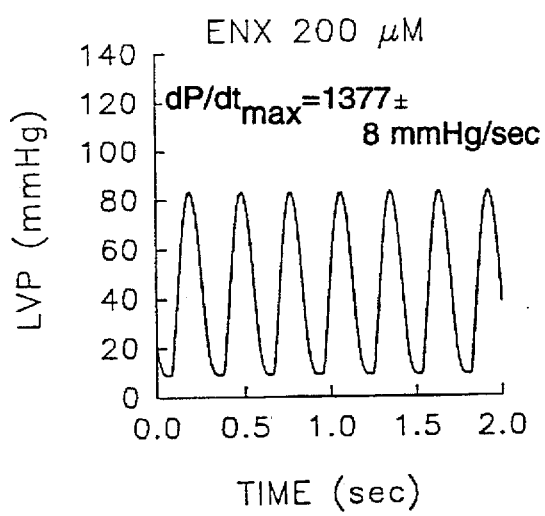
Figure 5D:
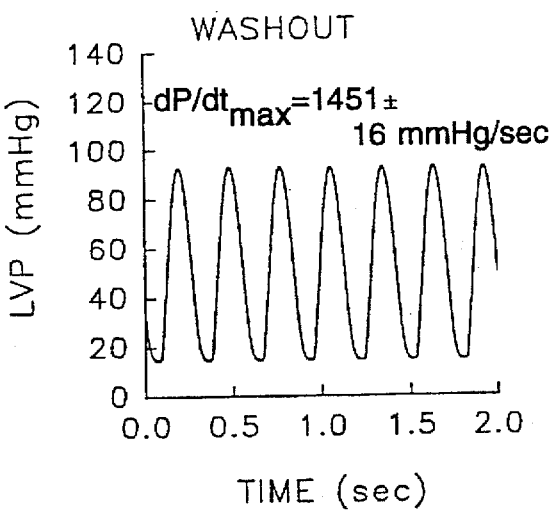

The synthesis of the optically pure 5-norbornen-2-yl amines involves the use of asymmetric Diels-Alder reactions to obtain intermediate carboxylic acids, followed by a Curtius rearrangement as described above. A general scheme for synthesizing these compounds is shown in FIG. 3.

Figure 9A:
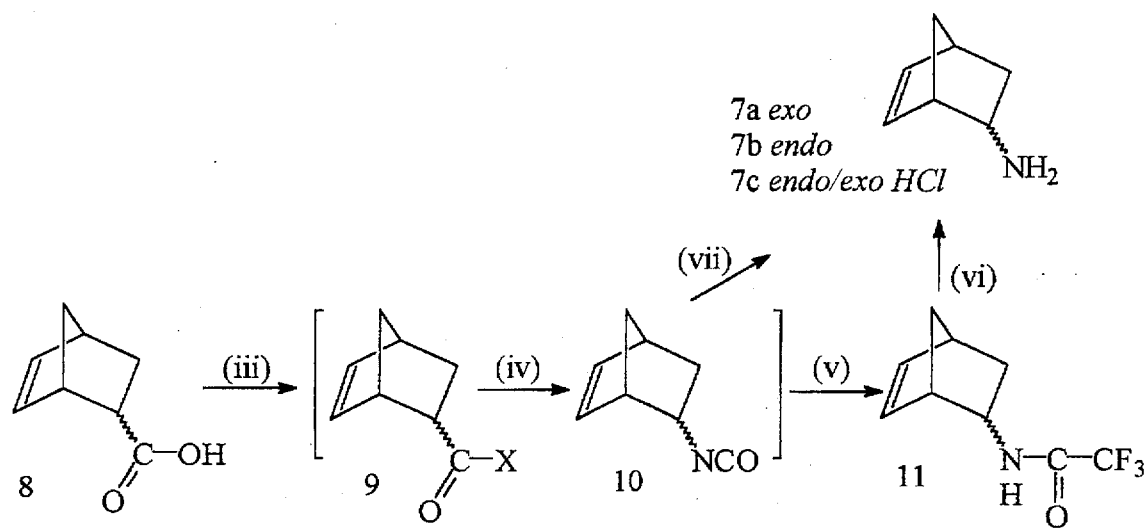
FIGS. 9A–9B show alternative schemes for the synthesis of exo- or endo-5-norborn-2-ene or endo/exo-5-norborn-2-ene hydrochloride. Legend: (i) KNCS, H$_2$SO$_4$; (ii) NaOH; (iii) SOCl$_2$/ClC(O)OEt, NEt$_3$; (iv) NaN$_3$, H$_2$O then $\Delta$; (v) TFA; (vi) K$_2$CO$_3$; (vii) NaN$_3$; H$_2$O, then 2M HCl/CCl$_4$.
Figure 9B:
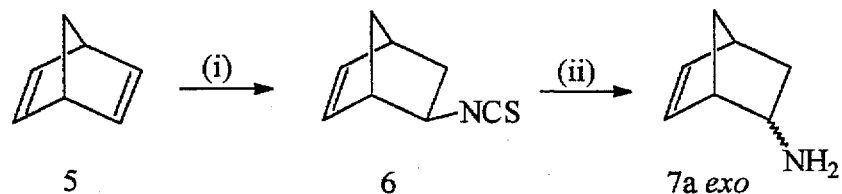

EXAMPLE 6
Analytical Data for Synthesis of $A_1$ Adenosine Receptor Agonists and Intermediates The reference numbers given for compounds described in this Example refer to FIGS. 9A and/or 9B. Melting points were determined on an electrothermal melting point apparatus and are uncorrected. $^1H$ and $^{13}C$ NMR spectra were recorded on a JEOL JNM-EX270 spectrometer. Unless otherwise stated, d6-DMSO was used as a solvent and TMS as an internal standard. The number of protons on each carbon was determined by DEPT experiments and is reported with the corresponding $^{13}C$ NMR signal. Infrared spectra were recorded as KBr discs on a Bio-Rad 3240-SPC spectrophotometer. FAB mass spectra were measured on a JEOL JMS-DX300 mass spectrometer and processed on an MSS data system. Merck Kieselgel 60 and 60 $F_{254}$ were used for column and thin layer chromatography, respectively. Solvents were either AR grade or distilled prior to use. Acetone was dried by distillation over potassium carbonate and was stored over 4 Å sieves.

$N^6$-(exo-5,6-epoxynorborn-2-yl) adenosine. Dimethyldioxirane in acetone (40.0 mL, ≈0.1M, ≈4.0 mmol) was added dropwise to a solution of $N^6$-(exo-norborn-5-en-2yl) adenosine (0.5 g, 1.39 mmol) in dry methanol (100 mL) at 0°–5° C. The reaction mixture was stirred for 8 hours at 0°–5° C. and then 12 hours (overnight) at room temperature. The solvent was evaporated under reduced pressure and the crude product purified by column chromatography ($CHCl_3$/ $MeOH/NH_3$, 80:20:1) to yield a white crystalline product (0.42 g, 80%); mp 240°–242° C.; $_1H$ NMR: δ1.15 (m, 2H, H3"/H7"), 1.72 (m, 2H, H3"/H7"), 2.41 (br s, 1H, H1'/H4"), 2.51 (br s, 1H, H1'/H4"), 3.18 (m, 2H, H2", H5", H6"), 3.64 (m, 2H, H5a',b'), 4.00 (d, 1H, H4'), 4.18 (d, 1H, H3'), 4.64 (m, 1H, H2'), 5.24 (br s, 1H, OH), 5.50 (br s, 2H, 2×OH), 5.92 (d, 1H, H1'), 7.88 (d, 1H, NH), 8.26 (s, 1H, H2/8), 8.38 (s, 1H, H2/8); $^{13}C$ NMR: δ23.0, 34.3, 36.3, 42.7, 49.1, 49.6, 51.0, 61.8, 70.8, 73.7, 86.0, 88.1, 119.8, 139.9, 148.6, 152.4, 154.1; HR MS ($C_{17}H_{22}N_5O_5$) calc. 376.16208, found 376.16109).

$N^6$-(endo-5,6-epoxynorborn-2-yl) adenosine. Dimethyldioxirane in acetone (27.8 mL, ≈0.1M, ≈2.78 mmol) was added dropwise to a solution of $N^6$-(endo-5,6-norborn-5-en-2-yl) adenosine (0.5 g, 1.39 mmol) in dry methanol (40 mL) at 0°–5° C. The reaction mixture was stirred for 4 hours at 0°–5° C. and then 2 hours at room temperature. The solvent was evaporated under reduced pressure and the crude product purified by column chromatography (EtOAc/MeOH/ $NH_3$, 90:10:1:) to yield a white crystalline product (0.36 g, 68%); mp 207°–214° C. (dec.); $^1H$ NMR: δ0.93–2.08 (m, 4H, H3", H7"), 2.42 (br s, 1H, H1"/H4"), 2.87 (br s, 1H, H1"/H4"), 3.23–3.41 (m, 3H, H2", H6"), 3.68 (dd, 2H, H5'), 4.03 (d, 1H, H4'), 4.22 (br s, 1H, H3'), 4.67 (br s, 1H, H2'), 5.22 (br s, 1H, OH), 5.44 (br s, 2H, 2×OH), 5.97 (d, 1H, H1'), 7.84 (br s, 1H, NH), 8.25 (s, 1H, H2/8), 8.38 (s, 1H, H2/8); $^{13}C$ NMR: δ25.2; 31.1, 36.4, 39.5, 48.3, 50.7, 61.6, 70.6, 73.4, 85.8, 87.9, 120.0, 139.7, 148.3, 152.2, 154.7; HR MS ($C_{17}H_{22}N_5O_5$) calc. 376.16208, found 376.16228.

$N^6$-(exo-norborn-5-en-2-yl) adenosine. A solution of exo-5-aminonorborn-2-ene (2.02 g, 18.5 mmol) in dry methanol (20 mL) was added to a solution of 6-chloropurine riboside (5.0 g, 17.4 mmol) and triethylamine (3.53 g, 34.9 mmol) in dry methanol (40 mL). After 24 hours reflux, another molar equivalent of exo-5-aminonorborn-2-ene was added, and refluxing was continued for a further 40 hours. After evaporation of the solvent and excess triethylamine, the crude product was purified by column chromatography using $CHCl_3/MeOH/NH_3$ (80:20:1) as an eluent). Pure 4a was isolated in 98% yield; mp 108°–113° C.; $^1H$ NMR: δ1.37–1.73 (m, 4H, H3", H7"), 2.78 (br s, 1H, H1"/H4"), 2.83 (br s, 1H, H4"), 3.20 (m, 1H, H2"), 3.62 (m, 2H, H5a',b'), 3.96 (d, 1H, H4'), 4.14 (d, 1H, H3'), 4.60 (m, 1H, H2'), 5.19 (d, 1H, OH), 5.44 (d, 2H, 2×OH), 5.89 (d, 1H, H1'), 6.16 (dd, 1H, H5/H6"), 6.20 (dd, 1H, H5"/H6"), 7.97 (br s, 1H, NH), 8.23 (br s, 1H, H2/8), 8.35 (s, 1H, H2/8); $^{13}C$ NMR: δ34.5, 41.5, 46.5, 48.3, 51.7, 62.4, 71.4, 74.5, 86.8, 89.0, 120.2, 135.4, 140.1, 140.7, 148.7, 153.4, 154.9.

$N^6$-(endo-norborn-5-en-2-yl) adenosine. 6-chloropurine riboside (0.70 g, 2.44 mmol) and endo-5-aminonorborn-2-ene (0.32 g, 2.93 mmol) were dissolved in dry methanol (20 mL) under an atmosphere of nitrogen. Triethylamine (0.51 mL), 0.37 g, 3.66 mmol) was added, and the reaction mixture was refluxed for 48 hours. After this period, HPLC monitoring indicated no further change was occurring, so the solvent was evaporated to yield a tan, oily solid. The compound was obtained as a white foam (0.69 g, 79%) after column chromatography with ethyl acetate/methanol/ ammonium hydroxide (90:10:1); mp 108°–112° C.; $^1H$ NMR: δ1.11–2.14 (m, 4H, H3", H"), 2.79 (br s, 1H, H1"/ H4"), 2.83 (br s, 1H, H1"/H4"), 3.22 (br s, 1H, H2"), 3.61 (m, 2H, H5a',b'), 3.97 (d, 1H, H4'), 4.15 (d, 1H, H3'), 4.61 (m, 1H, H2'), 5.20 (d, 1H, OH), 5.45 (d, 2H, 2×OH), 5.89 (d, 1H, 4H'), 5.97 (dd, 1H, H5"/H6"), 6.35 (dd, 1H, H5"/H6"), 6.93 (br s, 1H, NH), 8.25 (br s, 1H, H2/8), 8.36 (s, 1H, H2/8); $^{13}C$ NMR: δ33.5, 42.1, 45.5, 47.9, 50.4, 61.6, 70.6, 73.5, 85.8, 87.9, 119.6, 131.6, 138.8, 139.6, 148.2, 152.2, 154.4.

exo-Norborn-5-ene-2-yl isothiocyanate (6). Concentrated $H_2SO_4$ (38.4 g) in water (12 mL) was added dropwise over a 2-hour period to a mixture of bicyclo[2.2.1]hepta-2,5-diene (60 mL), benzene (150 mL), and KSCN (57.5 g) at 35°–40° C. After 3 hours, the reaction mixture was cooled and water was added. The reaction mixture was filtered through a glass fritted filter funnel under vacuum and rinsed with ether (200 mL). The organic layer was separated, washed with water, and dried over magnesium sulfate. Filtration and evaporation of the solvent yielded an orange liquid. Distillation under reduced pressure (70°–74° C., 1 mbar, lit.$^6$76°–78° C., 1 mmHg) yielded pure compound (40%); $^1H$ NMR: δ1.61–1.77 (m, 4H, H3, H7), 2.92 (br s, 1H, H1/H4), 3.10 (br s, 1H, H1/H4), 3.53 (t, 1H, H2), 5.98 (dd, 1H, H5/H6), 6.21 (dd, 1H, H5/H6); $^{13}C$ NMR: δ35.6, 41.0, 46.1, 49.8, 55.3, 132.7, 140.2.

exo-5-aminonorborn-2-ene (7a). To a stirred solution of the norbornyl isothiocyanate (56.7 g, 0.375 mmol) in ethylene glycol held at 100° C., solid NaOH (45.0 g) was added over a 5-minute period. The temperature was increased to 165° C. and the reaction was stirred for 3 hours. After cooling, the reaction mixture was then cooled and poured into a solution of saturated potassium carbonate (1 L) and then extracted with dichloromethane (3×400 mL). The organic layer was separated and then extracted with HCl (2N, 3×200 mL), made basic with 2N NaOH, and saturated with potassium carbonate. Filtration and evaporation of the solvent afforded a liquid which was distilled under vacuum (54°–54.5° C., 30 mmHg, lit.[7] 70° C., 40–41 mmHg) to yield a tan product (14.3 g, 35%). $^1$H NMR: δ0.88 (dd, 1, H2), 5.92 (dd, 1H, H5/H6), 5.96 (dd, 1H, H5/H6); $^{13}$C NMR (CDCl$_3$): δ37.0, 41.2, 44.8, 50.9, 51.9, 135.0, 138.0.

endo-5-aminonorborn-2-ene (7b). A mixture of 2-trifluoroacetylaminonorborn-5-ene (0.54 g, 2.6 mmol) and potassium carbonate (0.61 g, 4.4 mmol) in methanol (5 mL) and water (20 mL) were stirred at ambient temperature under an atmosphere of nitrogen for 25 hours. After concentration on a rotary evaporator, the reaction mixture was extracted with diethyl ether (3×20 mL). The organic phase was dried over magnesium sulfate, filtered, and evaporated to yield a tan oil (0.23 g, 80%). Distillation yielded pure 7b (152°–160° C., lit.[10] 150°–160° C.). $^1$H NMR: δ0.43 (dt, 1H, H3/H7), 1.20–1.30 (m, 2H, H3/H7), 1.95 (m, 1H, H3/H7), 2.72 (br s, 1H, H1/H4), 2.75 (br s, 1H, H1/H4), 3.28 (m, 1, H2), 5.97 (dd, 1H, H5/H6), 6.30 (dd, 1H, H5/H6); $^{13}$C NMR (CDCl$_3$): δ33.6, 42.6, 47.9, 48.5, 51.1, 131.6, 138.9.

exo/endo-5-aminonorborn-2-ene hydrochloride (7c). Method A (via acid chloride): A solution of norborn-5-ene-2-carbonyl chloride (2.66 g, 17.0 mmol) in CCl$_4$ (25 mL) containing tetrabutylammonium bromide (≈50 mg) was cooled in an ice bath. A solution of sodium azide (1.33 g, 20.5 mmol) in distilled water (5 mL) was added, and the reaction mixture was stirred vigorously for 2 hours at 0° C. The reaction mixture was poured onto ice (≈10 mL), and the aqueous phase was extracted with CCl$_4$ (2×25 mL). All organic portions were combined and refluxed with 2M HCl (8.5 mL) for 17 hours. After cooling, the aqueous phase was collected and the CCl$_4$ washed with 0.5M HCl (10 mL). Evaporation of the combined aqueous layers afforded a white solid (2.37 g, 96%). This solid was either purified by trituration with ethyl acetate or used directly for the synthesis of N$^6$-(endo-norborn-5-en-2-yl) adenosine. Method B (via mixed anhydride): A solution of norborn-5-ene-2-carboxylic acid (3.74 g, 27.1 mmol) and triethylamine (4.40 mL, 3.21 g, 31.7 mmol) in dry acetone (40 mL) was cooled in an ice bath. Freshly distilled ethyl chloroformate (2.98 mL, 3.38 g, 31.2 mmol) in acetone (15 mL) was added, and the reaction mixture was stirred for 30 minutes at 0° C. After this period, a solution of sodium azide (2.21 g, 34.0 mmol) in distilled water (10 mL) was added, and the reaction mixture was stirred for 2 hours at 0° C. The reaction mixture was poured onto ice (≈10 mL), and the aqueous phase was extracted with CCL$_4$ (2×25 mL). All organic portions were combined and refluxed with 2M HCl (13.6 mL) for 20 hours. After cooling, the aqueous phase was collected and the CCl$_4$ washed with 0.5M HCl (10 mL). Evaporation of the combined aqueous layers afforded an oily solid which was triturated with ethyl acetate (3.72 g, 94%); mp 256°–265° C. (dec.); $^1$H NMR: δ0.85–2.09 (m, H3 exo, endo, H7 exo, endo), 2.82 (br s, H1/H4 endo), 2.99 (br s, H1/H4 exo), 3.02 (br s, H1/H4 exo), 3.08 (br s, H1/H4 endo), 3.38 (m, H2 exo, endo), 5.96 (dd, H5/H6 endo), 6.05 (dd, H5/H6 exo), 6.20 (dd, H5/H6 exo), 6.37 (dd, H5/H6 endo), 8.03 (br s, NH$_2$), 8.50 (br s, HCl); $^{13}$C NMR: δ31.6, 40.8, 41.9, 44.7, 44.8, 45.2, 45.4, 47.9, 49.3, 50.2, 130.3, 133.9, 139.3, 140.4. Integration of the $^1$H NMR signals indicated that the mixture contained ≈85% of the endo-isomer.

exo/endo-norborn-5-ene-2-carbonyl chloride (9). A solution of 8 (3.5 g, 28.9 mmol) in thionyl chloride (2.7 mL, 35.2 mmol) under a nitrogen atmosphere was stirred overnight at room temperature. Excess thionyl chloride was evaporated under reduced pressure, and the resultant oil was distilled (65° C.C., 7.5 mmHg); $^1$H NMR (CDCl$_3$): δ1.32–1.56 (m, H3/H7 exo/endo), 1.95 (m, H3/H7 exo/endo), 2.98 (br s, H1/H4 exo/endo), 3.42 (dd, 1H, H5/H6 exo), 6.26 (dd, 1H, H5/H6 endo); $^{13}$C NMR (CDCl$_3$): δ30.0, 31.1, 41.7, 42.8, 42.9, 46.2, 46.8, 47.0, 49.1, 56.3, 131.5, 134.8, 138.6, 138.9, 174.8, 176.6.

2-trifluoroacetylaminonorborn-5-ene (11). Method A (via mixed anhydride): A solution of norborn-5-ene-2-carboxylic acid (1.75 g, 12.8 mmol) and triethylamine (1.95 mL, 1.43 g, 14.1 mmol) in dry acetone (25 mL) was cooled in an ice bath. Freshly distilled ethyl chloroformate (1.41 mL, 1.60 g, 14.7 mmol) was added, and the reaction mixture was stirred at 0° C. After this period, a solution of sodium azide (1.04 g, 16.0 mmol) in distilled water (5 mL) was added, and the reaction mixture was stirred for 2 hours at 0° C. The reaction mixture was poured onto ice (≈10 mL), and the aqueous phase was extracted with dichloromethane (2×20 mL). All organic portions were combined, dried over magnesium sulfate for 14 hours, filtered, and evaporated to yield a colorless oil. This oil was taken up in dichloromethane and refluxed with trifluoroacetic acid (1.28 mL, 1.90 g, 16.7 mmol) for 14 hours. After cooling, the reaction mixture was washed with saturated sodium bicarbonate (2×25 mL), dried over magnesium sulfate, filtered, and evaporated to afford the crude product. Purification was achieved by column chromatography using chloroform/hexane (1:1) as an eluent. The final product was obtained as a white crystalline solid (1.48 g, 57%). Method B (via acid chloride, single phase): A solution of norborn-5-ene-carbonyl chloride (1.90 g, 12.5 mmol) in acetone (25 mL) was cooled in an ice bath. A solution of sodium azide (0.98 g, 15.1 mmol) in distilled water (5 mL) was added, and the reaction mixture was stirred for 2 hours at 0° C. The reaction mixture was poured onto ice (≈10 mL), and the aqueous phase was extracted with dichloromethane (3×40 mL). All organic portions were combined, dried over magnesium sulfate for 14 hours and then filtered. Trifluoroacetic acid (1.25 mL, 1.85 g, 16.2 mmol) was added to the filtrate, which was then refluxed for 24 hours. After cooling, the reaction mixture was washed with saturated sodium bicarbonate (2×25 mL), dried over magnesium sulfate, filtered, and evaporated to an eluent. The final product was obtained as a white crystalline solid (1.41 g, 57%). Method C (via acid chloride, phase transfer conditions): A solution of norborn-5-ene-2-carbonyl chloride (2.0 g, 13.4 mmol) in dichloromethane (25 mL) containing tetrabutylammonium bromide (50–100 mg) was cooled in an ice bath. A solution of sodium azide (1.05 g, 16.2 mmol) in distilled water (5 mL) was added, and the reaction mixture was stirred vigorously for 2 hours at 0° C. The reaction mixture was poured onto ice (≈10 mL), and the aqueous phase was extracted with dichloromethane (2×20 mL). All organic portions were combined, dried over magnesium sulfate for 14 hours, and then filtered. Trifluoroacetic acid (1.14 mL, 1.69 g, 14.8 mmol) was added to the filtrate, which was then refluxed for 14 hours. After cooling, the reaction mixture was washed with saturated sodium bicarbonate (2×50 mL), dried over magnesium sulfate, filtered, and evaporated to yield the crude product. Purification was achieved by column chromatography using chloroform/hexane (1:1) as an eluent. Evaporation of selected fractions yielded pure endo-2-trifluoroacetylaminonorborn-5-ene (0.77 g, 28%), though the overall yield of both exo and endo isomers was 56% (1.46 g); mp 44°–46° C.; $^1$H NMR (CDCl$_3$): δ0.83 (dt, 2H, H3/H7), 1.37–1.57 (m, 2H, H3/H7), 2.28 (m, 1H, H3/H7), 2.93 (br s, 1H, H1/H4), 3.13 (br s, 1H, H1/H4), 4.53 (m, 1H, H2), 6.04 (dd, 1H, H5/6), 6.45 (dd, 1H, H5/6); $^{13}$C NMR (CDCl$_3$): δ35.2, 42.5, 45.8, 48.8, 50.0, 115.8 (q, J-288.1 Hz, —CF$_3$), 130.7, 141.0, 156.7 (q, J=36.6 Hz, C=O).

N$^6$-(exo-5,6-epoxynorborn-2-yl) adenosine-1-oxide (Formula XI). m-Chloroperbenzoic acid (216 mg, 1.25 mmol) was added to a solution of $N^6$-exo-norborn-5-en-yl adenosine (359 mg, 10 mmol, 1.0 eq) in dichloromethane (40 mL). The reaction was stirred at room temperature while being monitored by tlc. Additional m-chloroperbenzoic acid (173 mg, 1.0 mmol) was added after 24 hours and then again after 48 hours. After a further 24 hours, the solvent was evaporated to yield the crude product. Purification was effected via column chromatography using $CHCl_3$/MeOH/ $NH_3$ (80:20:1) as an eluent and yielded pure 5 (239 mg, 61%); mp 125°–132° C.; $^1$H NMR: δ1.15 (dd, 2H, H3/H7), 1.76–1.95 (m, H3/H7), 2.46 (br s, 1H, H1"/H4"), 2.55 (br s, 1H, H1"/H4"), 3.23 (m, 3H, H2", H5", H6"), 3.62 (m, 2H, H5a',b'), 3.95 (d, 1H, H4'), 4.15 (br s, 1H, H3'), 4.63 (s, 1H, H2'), 5.12 (br s, 1H, OH), 5.27 (d, 1H, OH), 5.72 (d, 1H, OH), 5.90 (d, 1H, H1'), 8.17 (br s, 1H, NH), 8.60 (s, 1H, H2/8), 8.65 (s, 1H, H2/8); $^{13}$C NMR: δ22.8, 34.8, 36.4, 43.8, 48.8, 50.7, 52.1, 61.1, 70.1, 73.8, 85.5, 87.4, 118.5, 142.2, 142.7, 142.8, 146.3. MS ($C_{17}H_{22}N_5O_6$) m/e 392.

EXAMPLE 7
Activity of Agonist Compounds

The agonist compounds were tested for their potency to inhibit (−)-isoproterenol stimulated cAMP accumulation in $DDT_1$ MF-2 (DDT) cells. This effect is mediated through the action of the $A_1$-adenosine receptor ($A_1AR$). For comparison purposes, the epoxides $N^6$-(5,6-epoxynorborn-2-yl) adenosine (R- and S-enantiomers of endo- and exo-compounds) and the N-1 oxide thereof were compared to the well established and potent $A_1AR$ agonist, $N^6$-cyclopentyladenosine (CPA).

Materials and Methods

Cell culture. $DDT_1$ MF-2 cells (American Type Culture Collection) were grown as monolayers in Dulbecco's Modified Eagle's Medium containing 5% fetal bovine serum, 100 U/mL penicillin G, 0.1 mg/mL streptomycin and 2.5 µg/mL amphotericin B in a water-humidified 5% $CO_2$ and 95% air mixture at 37° C. Cells were seeded at $0.2-1.0\times10^4$ cells/ $cm^2$ and subcultured twice weekly after detachment using divalent cation-free phosphate-buffered saline containing 1 mM ethylenediamine tetraacetic acid (EDTA). Experiments were performed on cells that were grown to 1 day preconfluent.

cAMP determinations. The potency of the $A_1AR$ agonists was determined by their ability to inhibit (−)-isoproterenol-stimulated cAMP accumulation. DDT cells were detached by incubation in 5 mL of divalent cation-free Hank's Balanced Salt Solution containing 1 mM EDTA. The cell suspension was centrifuged at 500 g for 5 minutes, washed once more by gentle resuspension and centrifugation, and resuspended in HBSS. The cells (0.15–2 mg protein) were then incubated in microfuge tubes with 0.5 mL HBSS containing 100 µM rolipram, 1 µM (−)-isoproterenol, and varying concentrations of the adenosine receptor agonists (0.05–1000 nM) for 10 minutes at 37° C. At the end of the incubation, the reaction was terminated by placing the tubes in a boiling water bath for 5 minutes. After cooling to room temperature, the tubes were centrifuged for 2 minutes at 10,000 g, and supernatants were saved. The protein content of the cells was determined by the method of Lowry et al. (Lowry, O. H., N. J. Rosebrough, A. L. Farr, R. J. Randall [1951] *J. Biol. Chem.* 193:265–275) using bovine serum albumin as standard.

The cAMP content of the supernatants was determined by a competitive protein binding assay as described previously (Standifer, K. M., J. Pitha, S. P. Baker [1989] *Naunyn-Schmiedeberg's Arch. Pharmacol.* 339:129–137). Briefly, an aliquot of the supernatant (50 µL) was incubated in a volume of 0.2 mL containing 25 mM Tris-HCl buffer (pH 7.0), 8 mM theophylline, 0.8 pmol [$^3$H]cAMP (31.4 Ci/mmol, New England Nuclear) and 20 µg of bovine heart cAMP dependent protein kinase (Sigma Chemical Co.) at 4° C. for 1 hour. At the end of the incubation, 75 µl of a 50% (v/v) hydroxyapatite-water suspension was added to each tube followed by 4 ml of ice-cold 10 mM Tris-HCl buffer (pH 7.0). The suspension was then poured onto a Whatman GF/B glass fiber filter under reduced pressure, the filter was washed with a further 6 ml of ice-cold buffer, placed in a scintillation vial with 4 mL of Liquiscint (National Diagnostics), and the radioactivity determined in a liquid scintillation counter. The amount of cAMP in the samples was calculated from a standard curve using known concentrations of unlabeled cAMP. The effective concentration of compounds which give 50% inhibition of maximal cAMP accumulation were determined using a concentration effect analysis with non linear regression algorithm (Marquardt-Levenberg).

Results. (−)-Isoproterenol (1 µM) alone increased cAMP accumulation in DDT cells 57-fold above the basal level. CPA and the epoxide derivatives inhibited the (−)-isoproterenol stimulated cAMP accumulation in a concentration-dependent manner with the $EC_{50}$ values shown in Table 8, below. CPA and the racemic exo and endo isomers of $N^6$(5,6-epoxynorborn-2-yl) adenosine inhibited cAMP accumulation with similar $EC_{50}$ values of about 1–2 nM. In contrast, the N-oxide derivative of the exo isomer (12) was much less potent than CPA or the exo- and endo-isomers of $N^6$-(5,6-epoxynorborn-2-yl) adenosine with an $EC_{50}$ value of 403 nM.

TABLE 8

Agonist concentration which inhibited (−)-isoproterenol-stimulated cAMP accumulation by 50% ($EC_{50}$)

| Compound | $EC_{50}$ (nM)[a] |
|---|---|
| CPA | 1.7 ± 0.4 |
| $N^6$-(exo-5,6-epoxynorborn-2-yl) adenosine | 1.1 ± 0.2 |
| $N^6$-(endo-5,6-epoxynorborn-2-yl) adenosine | 1.0 ± 0.3 |
| $N^6$-(exo-5,6-epoxynorborn-2-yl) adenosine-1-oxide | 403 ± 46 |

[a]DDT cells were incubated with 1 µM (−)isoproterenol and various concentrations of the compounds for 10 minutes at 37° C. The cAMP accumulated and the $EC_{50}$ values were determined as described in the Experimental Section. Basal and (−)isoproterenol-stimulated cAMP accumulated were 8 ± 3 and 458 ± 41 pmol cAMP formed per 10 minutes, respectively. Each value is the mean ± SE of three separate determinations performed in triplicate.

EXAMPLE 8
Uses, Formulations, and Administrations

Therapeutic and prophylactic application of the subject compounds, and compositions comprising them, can be accomplished by any suitable method and technique presently or prospectively known to those skilled in the art. Further, the compounds of the invention have use as starting materials or intermediates for the preparation of other useful compounds and compositions. The compounds of the invention are useful for various non-therapeutic and therapeutic purposes. It is apparent from the testing that the compounds of the invention have effective antiarrhythmic activity. Specifically, they are useful in regulating cardiac arrhythmia, including PVST, in animals, more preferably in mammals, and most preferably in humans.

The demonstrated effects of both the agonists and the antagonists on cardiac chronotropy, dromotropy, and inotropy make them useful therapeutically as either stimulants or modulators of cardiac performance, thereby affecting function of the heart. For example, the regulation or modulation activity of the subject compounds can affect heart rate (chronotropic effect) and impulse conduction (dromotropic effect). The subject compounds can also be used diagnostically to determine parameters of cardiac function, e.g., as pharmacological reagents useful in determining whether adenosine receptors are mediators of dysfunction of the heart or other organs.

The subject compounds can also serve as standards for in vitro and in vivo studies that measure or compare activities of other agonists and antagonists that act directly or indirectly through adenosine receptors. As reagents for such comparisons, the compounds are valuable pharmacological tools. Their high affinity and selectivity for the $A_1$ adenosine receptor make them important sources of information about the function of those receptors throughout the body.

Other uses for the subject compounds include their use in the characterization of structure or location of adenosine receptors in organs or tissues. This can be done by, for example, attaching an appropriate label or reporter to the subject compounds by standard techniques or procedures known to persons of ordinary skill in the art. The labels that are suitable for conjugation to the compounds of the subject invention include, but are not limited to, radiolabels (e.g., radioisotopes), fluorescent labels, and biotin labels. Radioisotopes that are suitable for labeling the subject compounds include Bromine-77, Fluorine-18, Iodine-131, Iodine-123, Iodine-125, Iodine-126, Iodine-133, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Technetium-99m, Tellurium-121m, Tellurium-99m, Tellurium-125m, Thulium-165, Thulium-167, Thulium-168, and Tritium. The gamma-emitting Indium species and Technetium-99m are preferred isotopes because these isotopes are detectable with a gamma-camera and have favorable half lives for imaging in vivo. Alternatively, it would be recognized by those of ordinary skill in the art that non-radioactive labels, for example, enzyme-substrate complexes, e.g., biotin-avidin, horseradish peroxidase-alkaline phosphatase, and the like could be used. Also, fluorescent entities suitable for labeling the subject compounds include fluorescein sodium, fluorescein isothiocyanate, and Texas red sulfonyl chloride. As such, the compounds can be used to visualize, in vitro or in vivo, structure or function of organs or tissues in which the $A_1$ adenosine receptors are present.

A further embodiment of the subject invention involves the use of the compounds to direct therapeutic compounds to the $A_1$ adenosine receptor site. Because of the specificity of the compounds of the subject invention, they can be conjugated to therapeutic compounds in order to direct the therapeutic compound to the vicinity of $A_1$ adenosine receptor. Also, in the case of compounds of the subject inventions which have selectivity to a specific type of tissue, such as heart tissue, these compounds can be used to direct therapeutic or diagnostic reagents to those locations.

The administration of the subject compounds of the invention is useful as an antiarrhythmic agent. Thus, pharmaceutical compositions containing compounds of the invention as active ingredients are useful in prophylactic or therapeutic treatment of cardiac arrhythmias in humans or other mammals.

The dosage administered will be dependent upon the antiarrhythmic response desired; the type of patient involved; its age, health, weight, kind of concurrent treatment, if any; frequency of treatment; therapeutic ratio and like considerations. Advantageously, dosage levels of the administered active ingredients can be, for examples, dermal, 1 to about 500 mg/kg; orally, 0.01 to 200 mg/kg; intranasal 0.01 to about 100 mg/kg; and aerosol 0.01 to about 50 mg/kg of animal body weight.

Expressed in terms of concentration, the active ingredient of the invention can be present in the new compositions for use dermally, transdermally, intranasally, bronchially, intramuscularly, intravaginally, intravenously, or orally in a concentration of from about 0.01 to about 50% w/w of the composition, and especially from about 0.1 to about 30% w/w of the composition. Preferably, the novel compound is present in a composition from about 1 to about 10% and, most preferably, the novel composition comprises about 5% novel compound.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

In accordance with the invention, pharmaceutical compositions comprise, as an active ingredient, an effective amount of one or more non-toxic, pharmaceutically acceptable ingredient(s). Examples of such ingredients for use in the compositions include ethanol, dimethyl sulfoxide, glycerol, alumina, starch, calcium carbonate, talc, flour, and equivalent non-toxic carriers and diluents.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An adenosine epoxide compound which selectively and specifically binds an $A_1$ adenosine receptor to act as an agonist of said receptor, wherein said compound is an $N^6$-(epoxycycloalkyl) adenosine.

2. The compound, according to claim 1, wherein said compound has the formula

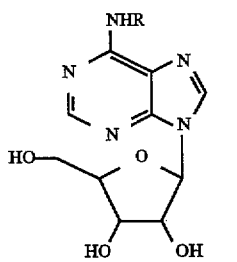

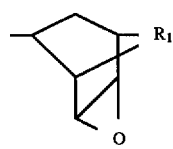

or

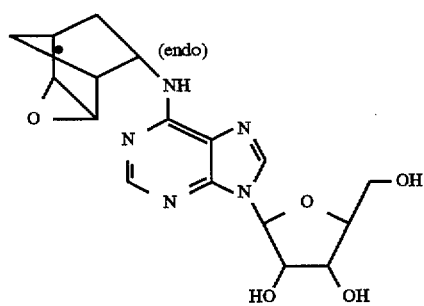

wherein $R_1$=alkyl of 1–4 carbons.

3. The compound, according to claim 1, wherein said compound is an $N^6$-(epoxynorbornyl) adenosine.

4. The compound, according to claim 1, wherein said compound has a formula selected from the group consisting of:

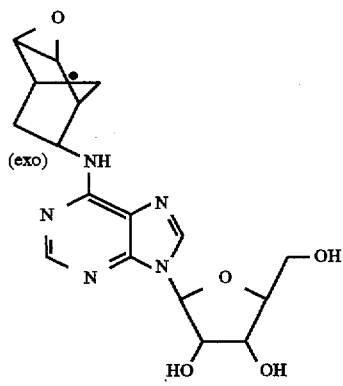

(VII)

(VIII)

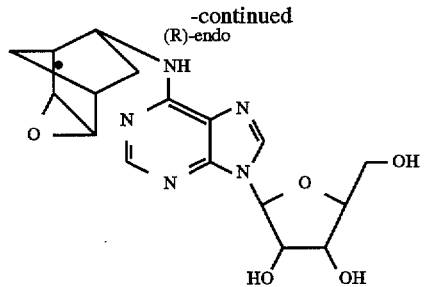

(IX)

(X)

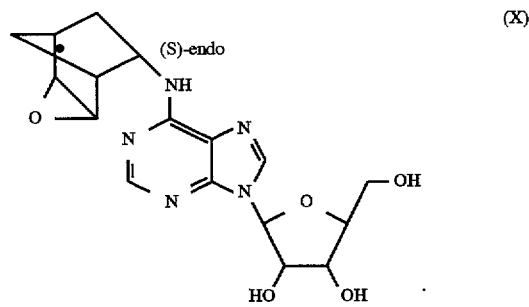

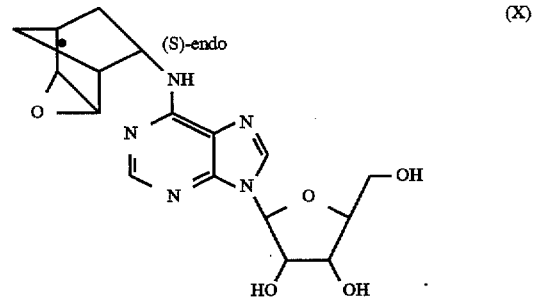

5. The compound, according to claim 1, wherein said compound has the structure:

(X)

6. A composition for use as an agonist of an $A_1$ adenosine receptor, said composition comprising an $N^6$-(epoxycycloalkyl) adenosine compound, or an analog, derivative, or isomer thereof; and a pharmaceutically acceptable carrier.

7. The composition, according to claim 6, wherein said compound has the formula:

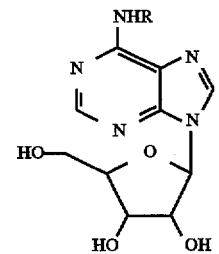

wherein $R$ = or

-continued
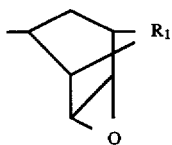
wherein $R_1$=alkyl of 1-4 carbons.
8. The composition, according to claim 6, wherein said compound is an $N^6$-(epoxynorbornyl) adenosine.
9. The composition, according to claim 6, wherein said compound has a formula selected from the group consisting of:
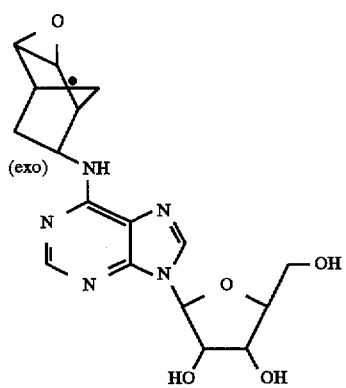
(VII)
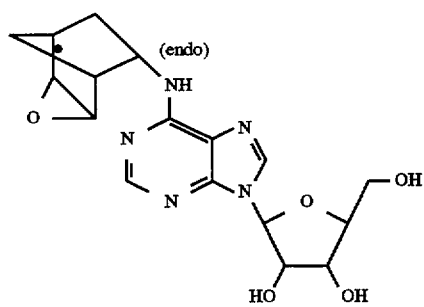
(VIII)
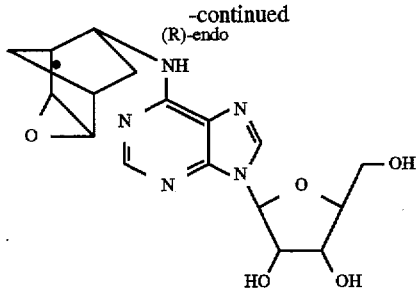
(IX)
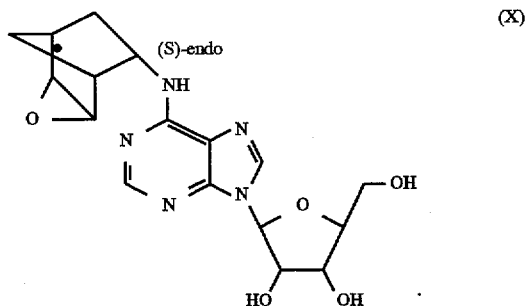
(X)
10. The composition, according to claim 6, wherein said compound has the formula:
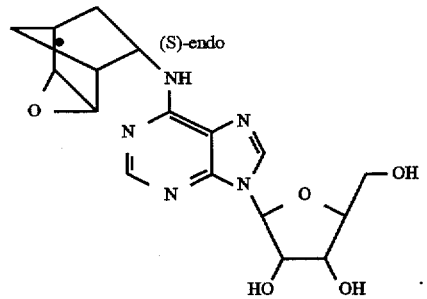
(X)
* * * * *

UNITED STATES PATENT AND TRADEMARK OFFICE
CERTIFICATE OF CORRECTION

PATENT NO. : 5,736,528
DATED : April 7, 1998
INVENTOR(S) : Balardinelli, et al

It is certified that error appears in the above-identified patent and that said Letters Patent is hereby corrected as shown below:

Column 2, lines 52-53: "$[3.1.2.0^{2}\cdot_{4}]$" should read --$[3.1.2.0^{2,4}]$--.

Column 9, line 2 (structure): "(IV)" should read --(VI)--.

Column 16, line 42 (Table 4): "0.45 ± 0.22 (5)" should read --0.45 ± 0.02 (5)--; and line 47: "$MF_{2\ cells.\ A2}$ receptor" should read --$MF_2$ cells. $A_2$ receptor--.

Column 18, line 53-54 "c/s-1, 4-dichlorobutene" should read --cis-1,4-dichlorobutene--.

Column 19, line 33: "2yl)" should read --2-yl)--.

Column 20, line 13: "br s, 1H, H4")" should read --(br s, 1H, H1"/H4")--; and line 16: "(dd, 1H, H5/H6")" should read --(dd, 1H, H5"/H6")--.

UNITED STATES PATENT AND TRADEMARK OFFICE
CERTIFICATE OF CORRECTION

PATENT NO. : 5,736,528
DATED : April 7, 1998
INVENTOR(S) : Balardinelli, et al

It is certified that error appears in the above-identified patent and that said Letters Patent is hereby corrected as shown below:

*In the Claims*

Column 28, lines 44-45 (Claim 6): "A composition for use as an agonist of an A1 adenosine receptor, said composition comprising an N6-(epoxycycloalkyl) adenosine compound, or an analog, derivative, or isomer thereof; and a pharmaceutically acceptable carrier." should read --A composition for use as an agonist of an $A^1$ denosine receptor, said composition comprising an $N^6$ (epoxycycloalkyl) adenosine compound and a pharmaceutically acceptable carrier.--

Signed and Sealed this

Thirteenth Day of October 1998

*Attest:*

BRUCE LEHMAN

*Attesting Officer*     Commissioner of Patents and Trademarks

UNITED STATES PATENT AND TRADEMARK OFFICE
CERTIFICATE OF CORRECTION

PATENT NO. : 5,736,528
DATED : April 7, 1998
INVENTOR(S) : Belardinelli *et al.*

It is certified that error appears in the above-identified patent and that said Letters Patent is hereby corrected as shown below:

Column 2, lines 52-53: "[3.1.2.0$^2$,$_4$]" should read --[3.1.2.0$^{2,4}$]--.

Column 9, line 2 (structure): "(IV)" should read --(VI)--.

Column 16, line 42 (Table 4): "0.45 ± 0.22 (5)" should read --0.45 ± 0.02 (5)--; and line 47: "MF$_{2\ cells.\ A2}$ receptor" should read --MF$_2$ cells. A$_2$ receptor--.

Column 18, line 53-54: "c/s-1, 4-dichlorobutene" should read --*cis*-1,4-dichlorobutene--.

Column 19, line 33: "2yl)" should read --2-yl)--.

Column 20, line 13: "br s, 1H, H4")" should read --(br s, 1H, H1"/H4")--; and line 16: "(dd, 1H, H5/H6")" should read --(dd, 1H, H5"/H6")--.

UNITED STATES PATENT AND TRADEMARK OFFICE
CERTIFICATE OF CORRECTION

PATENT NO. : 5,736,528
DATED : April 7, 1998
INVENTOR(S) : Belardinelli et al.

It is certified that error appears in the above-identified patent and that said Letters Patent is hereby corrected as shown below:

Column 28, lines 44-45 (Claim 6): "A composition for use as an agonist of an A1 adenosine receptor, said composition comprising an N6-(epoxycycloalkyl) adenosine compound, or an analog, derivative, or isomer thereof; and a pharmaceutically acceptable carrier." should read --A composition for use as an agonist of an $A1$ adenosine receptor, said composition comprising an $N^6$-(epoxycycloalkyl) adenosine compound and a pharmaceutically acceptable carrier.--

This certificate supersedes certificate of correction issued October 13, 1998

Signed and Sealed this

Eleventh Day of May, 1999

Q. TODD DICKINSON

Attest:

Attesting Officer

Acting Commissioner of Patents and Trademarks